US012708384B2

(12) United States Patent
Nguyen et al.

(10) Patent No.: US 12,708,384 B2
(45) Date of Patent: Aug. 18, 2026

(54) SYSTEM FOR TREATING OCCLUSIONS IN BODY LUMENS

(71) Applicant: Shockwave Medical, Inc., Santa Clara, CA (US)

(72) Inventors: Hoa D. Nguyen, San Jose, CA (US); Camilo Perez Saaibi, Fremont, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 54 days.

(21) Appl. No.: 18/883,250

(22) Filed: Sep. 12, 2024

(65) Prior Publication Data

US 2025/0000531 A1 Jan. 2, 2025

Related U.S. Application Data

(62) Division of application No. 18/104,170, filed on Jan. 31, 2023, now Pat. No. 12,114,874, which is a (Continued)

(51) Int. Cl.
*A61B 17/22* (2006.01)
*A61M 25/10* (2013.01)
*A61B 17/00* (2006.01)

(52) U.S. Cl.
CPC ..... *A61B 17/22012* (2013.01); *A61M 25/104* (2013.01); *A61B 2017/00154* (2013.01); (Continued)

(58) Field of Classification Search
CPC .......... A61B 17/22022; A61B 17/2204; A61B 17/22012; A61B 2017/22007; (Continued)

(56) References Cited

U.S. PATENT DOCUMENTS 2,916,647 A 12/1959 George
3,051,862 A 8/1962 Hoff
(Continued)

FOREIGN PATENT DOCUMENTS

AU 2009313507 B2 11/2014
AU 2013284490 B2 5/2018
(Continued)

OTHER PUBLICATIONS

Translation of DE-202006014285 (Year: 2006).*
(Continued)

*Primary Examiner* — Kathleen S Holwerda
(74) *Attorney, Agent, or Firm* — Morrison & Foerster LLP

(57) ABSTRACT

The invention provides a system for treating an occlusion within a body lumen. The system may comprise an insulated outer sheath; an elongated conductive tube, wherein the insulated outer sheath is circumferentially mounted around the elongated conductive tube; and an insulated wire having a helically coiled portion at a distal end of the insulated wire. The coiled portion includes an exposed distal tip, and a distal portion of the elongated conductive tube is circumferentially mounted around the distal coiled portion of the insulated wire. When a voltage is applied across the insulated wire and the elongated conductive tube, a current is configured to flow from the exposed distal tip of the insulated wire to the elongated conductive tube to generate a plurality of cavitation bubbles. In an alternate embodiment, an elongated central electrode is used in place of the conductive tube.

18 Claims, 8 Drawing Sheets

Related U.S. Application Data division of application No. 16/436,186, filed on Jun. 10, 2019, now Pat. No. 11,596,423.

(60) Provisional application No. 62/688,110, filed on Jun. 21, 2018.

(52) U.S. Cl.
CPC ............... *A61B 2017/22001* (2013.01); *A61B 2017/22007* (2013.01); *A61B 2017/22011* (2013.01); *A61B 2017/22021* (2013.01); *A61B 2017/22025* (2013.01); *A61B 2017/22042* (2013.01); *A61B 2017/22051* (2013.01); *A61B 2017/22094* (2013.01)

(58) Field of Classification Search
CPC A61B 2017/22008; A61B 2017/22009; A61B 2017/22011; A61B 2017/22024; A61B 2017/22025; A61M 25/104
See application file for complete search history.

(56) References Cited

U.S. PATENT DOCUMENTS 3,412,288 A 11/1968 Ostrander
3,413,976 A 12/1968 Roze
3,524,101 A 8/1970 Barbini
3,583,766 A 6/1971 Padberg
3,785,382 A 1/1974 Schmidt-Kloiber et al.
3,902,499 A 9/1975 Shene
3,942,531 A 3/1976 Hoff et al.
4,027,674 A 6/1977 Tessler et al.
4,030,505 A * 6/1977 Tessler ............. A61B 17/22022 604/105
4,445,509 A 5/1984 Auth
4,662,126 A 5/1987 Malcolm
4,662,375 A 5/1987 Hepp et al.
4,671,254 A 6/1987 Fair
4,685,458 A 8/1987 Leckrone
4,741,405 A 5/1988 Moeny et al.
4,809,682 A 3/1989 Forssmann et al.
4,813,934 A 3/1989 Engelson et al.
4,870,953 A 10/1989 DonMicheal et al.
4,878,495 A 11/1989 Grayzel
4,890,603 A 1/1990 Filler
4,900,303 A 2/1990 Lemelson
4,990,134 A 2/1991 Auth
4,994,032 A 2/1991 Sugiyama et al.
5,009,232 A 4/1991 Hassler et al.
5,046,503 A 9/1991 Schneiderman
5,057,103 A 10/1991 Davis
5,057,106 A 10/1991 Kasevich et al.
5,061,240 A 10/1991 Cherian
5,078,717 A 1/1992 Parins et al.
5,102,402 A 4/1992 Dror et al.
5,103,556 A 4/1992 Filip et al.
5,103,804 A 4/1992 Abele et al.
5,116,227 A 5/1992 Levy
5,125,928 A 6/1992 Parins et al.
5,150,717 A 9/1992 Rosen et al.
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Muller et al.
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,321,715 A 6/1994 Trost
5,324,255 A 6/1994 Passafaro et al.
5,336,234 A 8/1994 Vigil et al.
5,362,309 A 11/1994 Carter
5,364,393 A 11/1994 Auth et al.
5,368,591 A 11/1994 Lennox et al.
5,395,335 A 3/1995 Jang
5,417,208 A 5/1995 Winkler
5,425,735 A 6/1995 Rosen et al.
5,454,809 A 10/1995 Janssen
5,472,406 A 12/1995 de la Torre et al.
5,582,578 A 12/1996 Zhong et al.
5,584,843 A 12/1996 Wulfman et al.
5,603,731 A 2/1997 Whitney
5,609,606 A 3/1997 O'Boyle
5,662,590 A 9/1997 de la Torre et al.
5,697,281 A 12/1997 Eggers et al.
5,709,676 A 1/1998 Alt
5,735,811 A 4/1998 Brisken
5,846,218 A 12/1998 Brisken et al.
5,891,089 A 4/1999 Katz et al.
5,893,840 A 4/1999 Hull et al.
5,931,805 A 8/1999 Brisken
6,007,530 A 12/1999 Dornhofer et al.
6,027,501 A * 2/2000 Goble ................ A61B 18/1482 606/41
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster et al.
6,096,000 A 8/2000 Tachibana et al.
6,113,560 A 9/2000 Simnacher
6,132,444 A 10/2000 Shturman et al.
6,146,358 A 11/2000 Rowe
6,186,963 B1 2/2001 Schwarze et al.
6,210,404 B1 4/2001 Shadduck
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,398,792 B1 6/2002 O'Connor
6,406,486 B1 6/2002 De La Torre et al.
6,440,124 B1 8/2002 Esch et al.
6,494,890 B1 12/2002 Shturman et al.
6,514,203 B2 2/2003 Bukshpan
6,524,251 B2 2/2003 Rabiner et al.
6,589,253 B1 7/2003 Cornish et al.
6,607,003 B1 8/2003 Wilson
6,638,246 B1 10/2003 Naimark et al.
6,652,547 B2 11/2003 Rabiner et al.
6,666,834 B2 12/2003 Restle et al.
6,689,089 B1 2/2004 Tiedtke et al.
6,736,784 B1 5/2004 Menne et al.
6,740,081 B2 5/2004 Hilal
6,755,821 B1 6/2004 Fry
6,849,994 B1 * 2/2005 White ..................... H01T 13/56 313/125
6,855,123 B2 2/2005 Nita
6,939,320 B2 9/2005 Lennox
6,989,009 B2 1/2006 Lafontaine
7,066,904 B2 6/2006 Rosenthal et al.
7,087,061 B2 * 8/2006 Chernenko ........ A61B 18/1492 606/127
7,241,295 B2 7/2007 Maguire
7,309,324 B2 12/2007 Hayes et al.
7,389,148 B1 6/2008 Morgan
7,505,812 B1 3/2009 Eggers et al.
7,569,032 B2 8/2009 Naimark et al.
7,850,685 B2 12/2010 Kunis et al.
7,853,332 B2 12/2010 Olsen et al.
7,873,404 B1 1/2011 Patton
7,951,111 B2 5/2011 Drasler et al.
8,162,859 B2 4/2012 Schultheiss et al.
8,177,801 B2 5/2012 Kallok et al.
8,353,923 B2 1/2013 Shturman

(56) References Cited

U.S. PATENT DOCUMENTS 8,556,813 B2 10/2013 Cioanta et al.
8,574,247 B2 11/2013 Adams et al.
8,709,075 B2 4/2014 Adams et al.
8,728,091 B2 5/2014 Hakala et al.
8,747,416 B2 6/2014 Hakala et al.
8,856,371 B2 10/2014 Kariti et al.
8,888,788 B2 11/2014 Hakala et al.
8,956,371 B2 2/2015 Hawkins et al.
8,956,374 B2 2/2015 Hawkins et al.
9,005,216 B2 4/2015 Hakala et al.
9,011,462 B2 4/2015 Adams et al.
9,011,463 B2 4/2015 Adams et al.
9,044,618 B2 6/2015 Hawkins et al.
9,044,619 B2 6/2015 Hawkins et al.
9,072,534 B2 7/2015 Adams et al.
9,138,249 B2 9/2015 Adams et al.
9,198,825 B2 12/2015 Katragadda et al.
9,333,000 B2 5/2016 Hakala et al.
9,421,025 B2 8/2016 Hawkins et al.
9,433,428 B2 9/2016 Hakala et al.
9,522,012 B2 12/2016 Adams
9,642,673 B2 5/2017 Adams et al.
9,730,715 B2 8/2017 Adams
9,993,292 B2 6/2018 Adams et al.
9,999,788 B2 6/2018 Gattiker et al.
10,039,561 B2 8/2018 Adams et al.
10,118,015 B2 11/2018 De La Rama et al.
10,149,690 B2 12/2018 Hawkins et al.
10,154,799 B2 12/2018 Van Der Weide et al.
10,159,505 B2 12/2018 Hakala et al.
10,206,698 B2 2/2019 Hakala et al.
10,226,265 B2 3/2019 Ku et al.
10,517,620 B2 12/2019 Adams
10,517,621 B1 12/2019 Adams
10,555,744 B2 2/2020 Nguyen et al.
10,682,178 B2 6/2020 Adams et al.
10,702,293 B2 7/2020 Adams et al.
10,709,462 B2 7/2020 Nguyen et al.
10,765,440 B2 9/2020 Tozzi
10,959,743 B2 3/2021 Adams et al.
10,973,538 B2 4/2021 Hakala et al.
11,000,299 B2 5/2021 Hawkins et al.
11,076,874 B2 8/2021 Hakala et al.
11,337,713 B2 5/2022 Nguyen et al.
11,432,834 B2 9/2022 Adams
11,478,261 B2 10/2022 Nguyen
11,534,187 B2 12/2022 Bonutti
11,596,423 B2 3/2023 Nguyen et al.
11,596,424 B2 3/2023 Hakala et al.
11,622,780 B2 4/2023 Nguyen et al.
11,696,799 B2 7/2023 Adams et al.
11,992,232 B2 5/2024 Nguyen
12,114,874 B2 10/2024 Nguyen et al.
12,402,897 B2 9/2025 Nguyen
2001/0037106 A1 11/2001 Shadduck
2001/0044596 A1 11/2001 Jaafar
2002/0042610 A1 4/2002 Sliwa et al.
2002/0045890 A1 4/2002 Celliers et al.
2002/0077643 A1 6/2002 Rabiner et al.
2002/0082553 A1 6/2002 Duchamp
2002/0095151 A1* 7/2002 Dahla .................. A61B 18/148 606/41
2002/0119116 A1* 8/2002 Sahatjian ................ A61L 27/52 604/113
2002/0177889 A1 11/2002 Brisken et al.
2003/0004434 A1 1/2003 Greco et al.
2003/0088262 A1 5/2003 Bonnette et al.
2003/0176873 A1 9/2003 Chernenko et al.
2003/0229370 A1 12/2003 Miller
2004/0006333 A1 1/2004 Arnold et al.
2004/0010249 A1 1/2004 Truckai et al.
2004/0044308 A1 3/2004 Naimark et al.
2004/0097963 A1 5/2004 Seddon
2004/0097996 A1 5/2004 Rabiner et al.
2004/0158150 A1 8/2004 Rabiner et al.
2004/0162508 A1 8/2004 Uebelacker
2004/0193046 A1 9/2004 Nash et al.
2004/0249401 A1 12/2004 Rabiner et al.
2004/0254570 A1 12/2004 Hadjicostis et al.
2005/0015953 A1 1/2005 Keidar
2005/0021013 A1 1/2005 Visuri et al.
2005/0059965 A1 3/2005 Eberl et al.
2005/0075662 A1 4/2005 Pedersen et al.
2005/0090888 A1 4/2005 Hines et al.
2005/0113722 A1 5/2005 Schultheiss
2005/0113822 A1 5/2005 Fuimaono et al.
2005/0171527 A1 8/2005 Bhola
2005/0228372 A1 10/2005 Truckai et al.
2005/0245866 A1 11/2005 Azizi
2005/0251131 A1 11/2005 Lesh
2006/0004286 A1 1/2006 Chang et al.
2006/0069424 A1 3/2006 Acosta et al.
2006/0074484 A1 4/2006 Huber
2006/0085054 A1 4/2006 Zikorus et al.
2006/0184076 A1* 8/2006 Gill .................. A61B 17/22012 601/3
2006/0190022 A1 8/2006 Beyar et al.
2006/0221528 A1 10/2006 Li et al.
2007/0016112 A1 1/2007 Schultheiss et al.
2007/0088380 A1 4/2007 Hirszowicz et al.
2007/0129667 A1 6/2007 Tiedtke et al.
2007/0149966 A1 6/2007 Dahla et al.
2007/0156129 A1 7/2007 Kovalcheck
2007/0239082 A1 10/2007 Schultheiss et al.
2007/0239253 A1 10/2007 Jagger et al.
2007/0244423 A1 10/2007 Zumeris et al.
2007/0250052 A1 10/2007 Wham
2007/0255270 A1 11/2007 Carney
2007/0282301 A1 12/2007 Segalescu et al.
2007/0299481 A1 12/2007 Syed et al.
2008/0033423 A1 2/2008 Peacock
2008/0097251 A1 4/2008 Babaev
2008/0188913 A1 8/2008 Stone et al.
2009/0041833 A1 2/2009 Bettinger et al.
2009/0177085 A1 7/2009 Maxwell et al.
2009/0227992 A1 9/2009 Nir et al.
2009/0230822 A1 9/2009 Kushculey et al.
2009/0247945 A1 10/2009 Levit et al.
2009/0254114 A1 10/2009 Hirszowicz et al.
2009/0299447 A1 12/2009 Jensen et al.
2010/0016862 A1 1/2010 Hawkins et al.
2010/0036294 A1 2/2010 Mantell et al.
2010/0094209 A1 4/2010 Drasler et al.
2010/0114020 A1 5/2010 Hawkins et al.
2010/0114065 A1 5/2010 Hawkins et al.
2010/0121322 A1 5/2010 Swanson
2010/0179424 A1 7/2010 Warnking et al.
2010/0286709 A1 11/2010 Diamant et al.
2010/0305565 A1 12/2010 Truckai et al.
2011/0034832 A1 2/2011 Cioanta et al.
2011/0118634 A1 5/2011 Golan
2011/0208185 A1 8/2011 Diamant et al.
2011/0257523 A1 10/2011 Hastings et al.
2011/0295227 A1 12/2011 Hawkins et al.
2012/0071889 A1 3/2012 Mantell et al.
2012/0095461 A1 4/2012 Herscher et al.
2012/0116289 A1 5/2012 Hawkins et al.
2012/0143177 A1 6/2012 Avitall et al.
2012/0157991 A1 6/2012 Christian
2012/0203255 A1 8/2012 Hawkins et al.
2012/0221013 A1 8/2012 Hawkins et al.
2012/0253358 A1 10/2012 Golan et al.
2013/0023802 A1 1/2013 McIntosh et al.
2013/0030431 A1 1/2013 Adams
2013/0041355 A1 2/2013 Heeren et al.
2013/0116714 A1 5/2013 Adams et al.
2013/0123694 A1 5/2013 Subramaniyan et al.
2013/0150874 A1 6/2013 Kassab
2013/0158453 A1 6/2013 Brouillette et al.
2013/0253622 A1 9/2013 Hooven
2014/0005576 A1* 1/2014 Adams .................. A61B 18/00 601/4
2014/0039513 A1* 2/2014 Hakala ............. A61B 17/22022 606/128

(56) References Cited

U.S. PATENT DOCUMENTS

2014/0046229 A1 2/2014 Hawkins et al.
2014/0155830 A1 6/2014 Bonnette et al.
2014/0214061 A1 7/2014 Adams et al.
2015/0238209 A1 8/2015 Hawkins et al.
2015/0320432 A1 11/2015 Adams
2016/0151081 A1 6/2016 Adams et al.
2016/0184570 A1 6/2016 Grace et al.
2016/0262784 A1 9/2016 Grace et al.
2016/0324534 A1 11/2016 Hawkins et al.
2017/0135709 A1 5/2017 Nguyen et al.
2017/0231649 A1 8/2017 Rabiner et al.
2017/0311965 A1 11/2017 Adams
2018/0098779 A1 4/2018 Betelia et al.
2018/0360482 A1 12/2018 Nguyen
2019/0069916 A1 3/2019 Hawkins et al.
2020/0085458 A1 3/2020 Nguyen et al.
2021/0007760 A1 1/2021 Reisin
2021/0085383 A1 3/2021 Vo et al.
2021/0282792 A1 9/2021 Adams et al.
2021/0338258 A1 11/2021 Hawkins et al.
2022/0015785 A1 1/2022 Hakala et al.
2022/0240958 A1 8/2022 Nguyen et al.
2023/0011207 A1 1/2023 Nguyen
2023/0043475 A1 2/2023 Adams
2023/0181203 A1 6/2023 Nguyen et al.
2024/0268843 A1 8/2024 Nguyen
2025/0359877 A1 11/2025 Nguyen

FOREIGN PATENT DOCUMENTS

CA 2104414 A1 2/1995
CN 1204242 A 1/1999
CN 1269708 A 10/2000
CN 1810211 A 8/2006
CN 1942145 A 4/2007
CN 101043914 A 9/2007
CN 101534737 A 9/2009
CN 102057422 A 5/2011
CN 102271748 A 12/2011
CN 102355856 A 2/2012
CN 102765785 A 11/2012
CN 203564304 U 4/2014
CN 104582597 A 4/2015
CN 107847259 A 3/2018
CN 109843204 A 6/2019
DE 3038445 A1 5/1982
DE 202006014285 U1 * 12/2006 .............. H01T 9/00
EP 442199 A2 8/1991
EP 571306 A1 11/1993
EP 623360 A1 11/1994
EP 647435 A1 4/1995
EP 2253884 A1 11/2010
EP 2359764 A1 8/2011
EP 2362798 B1 4/2014
JP S58-032754 A 2/1983
JP S60-191353 U 12/1985
JP S62-099210 U 6/1987
JP S62-275446 A 11/1987
JP H03-63059 A 3/1991
JP H06-125915 A 5/1994
JP H06-506373 A 7/1994
JP H07-47135 A 2/1995
JP H08-89511 A 4/1996
JP H10-99444 A 4/1998
JP H10-314177 A 12/1998
JP H10-513379 A 12/1998
JP 2002538932 A 11/2002
JP 2003500098 A 1/2003
JP 2004081374 A 3/2004
JP 2004357792 A 12/2004
JP 2005501597 A 1/2005
JP 2005095410 A 4/2005
JP 2005515825 A 6/2005
JP 2006516465 A 7/2006
JP 2007289707 A 11/2007
JP 2007532182 A 11/2007
JP 2008506447 A 3/2008
JP 2011513694 A 4/2011
JP 2011520248 A 7/2011
JP 2011524203 A 9/2011
JP 2011528963 A 12/2011
JP 2012505050 A 3/2012
JP 2012508042 A 4/2012
JP 2015522344 A 8/2015
JP 2015525657 A 9/2015
JP 2015528327 A 9/2015
JP 2016508851 A 3/2016
JP 6029828 B2 11/2016
JP 6081510 B2 2/2017
JP 2017035491 A 2/2017
JP 2020524032 A 8/2020
WO WO-1989011307 A1 11/1989
WO WO-1992003975 A1 3/1992
WO WO-1996024297 A1 8/1996
WO WO-1999000060 A1 1/1999
WO WO-1999002096 A1 1/1999
WO WO-2000051502 A1 9/2000
WO WO-2000056237 A2 9/2000
WO WO-2004069072 A2 8/2004
WO WO-2005034793 A2 4/2005
WO WO-2005099594 A1 10/2005
WO WO-2005102199 A1 11/2005
WO WO-2006006169 A2 1/2006
WO WO-2006127158 A2 11/2006
WO WO-2007088546 A2 8/2007
WO WO-2007149905 A2 12/2007
WO WO-2009121017 A1 10/2009
WO WO-2009126544 A1 10/2009
WO WO-2009136268 A2 11/2009
WO WO-2009152352 A2 12/2009
WO WO-2010014515 A2 2/2010
WO WO-2010014515 A3 8/2010
WO WO-2010054048 A3 9/2010
WO WO-2011006017 A1 1/2011
WO WO-2011094111 A2 8/2011
WO WO-2011143468 A2 11/2011
WO WO-2012025833 A2 3/2012
WO WO-2013059735 A1 4/2013
WO WO-2014025397 A1 2/2014
WO WO-2014025620 A1 2/2014
WO WO-2015017499 A1 2/2015
WO WO-2016109739 A1 7/2016
WO WO-2018067656 A1 4/2018
WO WO-2019099218 A1 5/2019
WO WO-2019152898 A1 8/2019
WO WO-2019245746 A1 12/2019

OTHER PUBLICATIONS

Advisory Action received for U.S. Appl. No. 13/615,107, mailed on Nov. 6, 2015, 3 pages.
Advisory Action Received for U.S. Appl. No. 12/482,995, mailed on Jun. 2, 2014, 3 pages.
Advisory Action Received for U.S. Appl. No. 12/482,995, mailed on Sep. 29, 2011, 2 pages.
Advisory Action Received for U.S. Appl. No. 12/581,295, mailed on Jul. 3, 2014, 3 pages.
Advisory Action Received for U.S. Appl. No. 13/049,199, mailed on Jun. 7, 2012, 3 pages.
Advisory Action received for U.S. Appl. No. 13/267,383, mailed on Jan. 6, 2014, 4 pages.
Bom et al., (1988). "Intra-Arterial Ultrasonic Imaging for Recanalization by Spark Erosion," Ultrasound in Medicine & Biology,14(4):257-261.
Cleveland et al., (2012). "Chapter 38: The Physics of Shock Wave Lithotripsy," Extracorporeal Shock Wave Lithotripsy, 4:317-332.
Connors et al., (2003). "Renal Nerves Mediate Changes in Contralateral Renal Blood Flow after Extracorporeal Shockwave Lithotripsy," Nephron Physiol, 95:67-75.
Decision of Appeals Notice received for Japanese Patent Application No. 2011-534914, mailed on Oct. 17, 2016, 4 pages.

(56) References Cited

OTHER PUBLICATIONS

Decision to Grant received for European Patent Application No. 13756766.5, mailed on May 27, 2016, 2 pages.
Decision to Grant received for European Patent Application No. 09825393.3, mailed on Mar. 13, 2014, 2 pages.
Decision to Grant received for Japanese Patent Application No. 2011-513694, mailed on Oct. 7, 2014, 3 pages (Official Copy Only) (See Communication under 37 CFR § 1.98(a) (3)).
Extended European Search Report (includes Supplementary European Search Report and Search Opinion) received for European Patent Application No. 09763640.1, mailed on Oct. 10, 2013, 5 pages.
Extended European Search Report and Search Opinion received for European Patent Application No. 09825393.3, mailed on Feb. 28, 2013, 6 pages.
Extended European Search Report received for European Patent Application No. 13827971.6, mailed on Apr. 12, 2016, 8 pages.
Final Office Action received for U.S. Appl. No. 12/482,995, mailed on Jul. 22, 2011, 14 pages.
Final Office Action received for U.S. Appl. No. 12/501,619, mailed on Feb. 21, 2012, 12 pages.
Final Office Action received for U.S. Appl. No. 12/611,997, mailed on Dec. 11, 2012, 9 pages.
Final Office Action received for U.S. Appl. No. 12/611,997, mailed on Nov. 10, 2011, 15 pages.
Final Office Action received for U.S. Appl. No. 13/049,199, mailed on Apr. 4, 2012, 10 pages.
Final Office Action received for U.S. Appl. No. 13/207,381, mailed on Nov. 2, 2012, 7 pages.
Final Office Action received for U.S. Appl. No. 14/271,342 mailed on Feb. 27, 2015, 7 pages.
Final Office Action received for U.S. Appl. No. 12/482,995, mailed on Feb. 20, 2014, 11 pages.
Final Office Action received for U.S. Appl. No. 12/581,295, mailed on Jun. 5, 2014, 14 pages.
Final Office Action received for U.S. Appl. No. 12/611,997, mailed on Oct. 24, 2013, 10 pages.
Final Office Action received for U.S. Appl. No. 13/049,199 mailed on Aug. 11, 2014, 8 pages.
Final Office Action received for U.S. Appl. No. 13/207,381, mailed on Nov. 7, 2013, 7 pages.
Final Office Action Received for U.S. Appl. No. 13/267,383, mailed on May 28, 2015, 12 pages.
Final Office Action received for U.S. Appl. No. 13/267,383, mailed on Oct. 25, 2013, 8 pages.
Final Office Action received for U.S. Appl. No. 13/534,658, mailed on Aug. 23, 2016, 11 pages.
Final Office Action received for U.S. Appl. No. 13/615,107 mailed on Sep. 1, 2015, 9 pages.
Final Office Action received for U.S. Appl. No. 13/646,570, mailed on Dec. 23, 2014, 10 pages.
Final Office Action received for U.S. Appl. No. 14/229,735, mailed on Aug. 27, 2015, 7 pages.
Final Office Action received for U.S. Appl. No. 14/273,063, mailed on Dec. 28, 2016, 11 pages.
Final Office Action received for U.S. Appl. No. 14/660,539, mailed on Aug. 3, 2017, 11 pages.
Gambihler et al., (1994). "Permeabilization of the Plasma Membrane of LI210 Mouse Leukemia Cells Using Lithotripter Shock Waves," The Journal of Membrane Biology, 141:267-275.
Grassi et al., (2012). "Novel Antihypertensive Therapies: Renal Sympathetic Nerve Ablation and Carotid Baroreceptor Stimulation," Curr Hypertens Rep, 14:567-572.
Intention to Grant received for European Patent Application No. 13756766.5, mailed on Jan. 8, 2016, 5 pages.
International Preliminary Report on Patentability received for PCT Patent Application No. PCT/US2009/047070, mailed on Dec. 23, 2010, 7 pages.
International Preliminary Report on Patentability received for PCT Patent Application No. PCT/US2009/063354, mailed on May 19, 2011, 6 pages.
International Preliminary Report on Patentability received for PCT Patent Application No. PCT/US2011/047070, mailed on Feb. 21, 2013, 7 pages.
International Preliminary Report on Patentability received for PCT Patent Application No. PCT/US2012/023172, mailed on Aug. 15, 2013, 6 pages.
International Preliminary Report on Patentability received for PCT Patent Application No. PCT/US2012/063925, mailed on May 22, 2014, 12 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987 issued on Nov. 20, 2014, 11 pages.
International Preliminary Report on Patentability received for PCT Patent Application No. PCT/US2013/048277 mailed on Jan. 8, 2015, 9 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533 mailed on Mar. 26, 2015, 10 pages.
International Preliminary Report on Patentability received for PCT Patent Application No. PCT/US2015/029088, mailed on Nov. 17, 2016, 8 pages.
International Preliminary Report on Patentability received for PCT Patent Application No. PCT/US2019/035750, mailed on Dec. 30, 2020, 11 pages.
International Search Report and Written Opinion Received for PCT Application No. PCT/US2018/034855, mailed on Aug. 23, 2018, 13 pages.
International Search Report and Written Opinion received for PCT Patent Application No. PCT/US2013/031805 mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2015/029088 mailed on Jul. 16, 2015, 13 pages.
International Search Report and Written Opinion received for PCT Patent Application No. PCT/US2016/060817, mailed on Feb. 20, 2017, 13 pages.
International Search Report and Written Opinion received for PCT Patent Application No. PCT/US2019/035750, mailed on Aug. 1, 2019, 21 pages.
International Search Report and Written Opinion received for PCT Patent Application No. PCT/US2020/051551, mailed on Jan. 11, 2021, 16 pages.
International Search Report received for PCT Patent Application No. PCT/US2009/047070, mailed on Jan. 19, 2010, 4 pages.
International Search Report received for PCT Patent Application No. PCT/US2009/063354, mailed on Jun. 11, 2010, 3 pages.
International Search Report received for PCT Patent Application No. PCT/US2012/023172, mailed on Sep. 28, 2012, 3 pages.
International Written Opinion received for PCT Patent Application No. PCT/US2009/063354, mailed on Jun. 11, 2010, 4 pages.
International Written Opinion received for PCT Patent Application No. PCT/US2011/047070, mailed on May 1, 2012, 5 pages.

(56) References Cited

OTHER PUBLICATIONS

International Search Report and Written Opinion received for PCT Patent Application No. PCT/US2021/071938, mailed on Jan. 18, 2022, 13 pages.
Kodama et al., (2002). "Shock wave-mediated molecular delivery into cells," Biochimica et Biophysica Acta, 1542:186-194.
Lauer et al., (1997). "Shock wave permeabilization as a new gene transfer method," Gene Therapy, 4:710-715.
Non Final Office Action received for U.S. Appl. No. 12/482,995, mailed on Aug. 13, 2014, 10 pages.
Non Final Office Action received for U.S. Appl. No. 12/482,995, mailed on Jul. 12, 2013, 11 pages.
Non Final Office Action received for U.S. Appl. No. 12/611,997, mailed on Nov. 26, 2014, 8 pages.
Non Final Office Action received for U.S. Appl. No. 13/207,381, mailed on Nov. 25, 2014, 5 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non Final Office Action received for U.S. Appl. No. 14/079,463, mailed on Mar. 4, 2014, 9 pages.
Non Final Office Action received for U.S. Appl. No. 12/482,995, mailed on Feb. 11, 2011, 27 pages.
Non Final Office Action received for U.S. Appl. No. 12/501,619, mailed on Nov. 3, 2011, 10 pages.
Non Final Office Action received for U.S. Appl. No. 12/611,997, mailed on Apr. 8, 2013, 9 pages.
Non Final Office Action received for U.S. Appl. No. 12/611,997, mailed on Aug. 24, 2012, 11 pages.
Non Final Office Action received for U.S. Appl. No. 12/611,997, mailed on Jun. 21, 2011, 13 pages.
Non Final Office Action received for U.S. Appl. No. 13/049,199, mailed on Dec. 12, 2011, 10 pages.
Non Final Office Action received for U.S. Appl. No. 13/207,381, mailed on Feb. 22, 2013, 7 pages.
Non Final Office Action received for U.S. Appl. No. 13/207,381, mailed on Jun. 12, 2012, 6 pages.
Non Final Office Action received for U.S. Appl. No. 13/534,658, mailed on Mar. 11, 2016, 12 pages.
Non Final Office Action received for U.S. Appl. No. 14/218,858, mailed on Mar. 30, 2016, 13 pages.
Non Final Office Action received for U.S. Appl. No. 14/515,130, mailed on Jan. 14, 2016, 16 pages.
Non-Final Office Action received for U.S. Appl. No. 12/501,619, mailed on Jan. 28, 2014, 10 pages.
Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Non-Final Office Action received for U.S. Appl. No. 12/611,997, mailed on Feb. 13, 2014, 9 pages.
Non-Final Office Action received for U.S. Appl. No. 13/049,199, mailed on Feb. 4, 2014, 8 pages.
Non-Final Office Action received for U.S. Appl. No. 13/207,381, mailed on Feb. 25, 2014, 8 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.
Non-Final Office Action received for U.S. Appl. No. 13/615,107, mailed on Apr. 24, 2015, 9 pages.
Non-Final Office Action received for U.S. Appl. No. 13/646,583, mailed on Oct. 31, 2014, 8 pages.
Non-Final Office Action received for U.S. Appl. No. 14/061,554, mailed on Mar. 12, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Non-Final Office Action received for U.S. Appl. No. 14/273,063, mailed on Jun. 3, 2016, 9 pages.
Non-Final Office Action received for U.S. Appl. No. 14/660,539, mailed on Nov. 24, 2017, 10 pages.
Non-Final Office Action received for U.S. Appl. No. 14/693,155, mailed on Jan. 15, 2016, 6 pages.
Non-Final Office Action received for U.S. Appl. No. 15/474,885, mailed on Oct. 5, 2017, 9 pages.
Non-Final Office Action received for U.S. Appl. No. 15/652,070, mailed on Jan. 11, 2019, 9 pages.
Non-Final Office Action received for U.S. Appl. No. 14/660,539, mailed on Mar. 6, 2017, 14 pages.
Non-Final Office Action received for U.S. Appl. No. 16/436,186, mailed on Sep. 21, 2021, 16 pages.
Non-Final Office Action received for U.S. Appl. No. 16/436,186, mailed on Jun. 10, 2022, 14 pages.
Non-Final Office Action received for U.S. Appl. No. 17/025,866, mailed on Mar. 2, 2022, 9 pages.
Notice of Acceptance Received for Australian Patent Application No. 2009257368, mailed on Aug. 28, 2014, 2 pages.
Notice of Acceptance Received for Australian Patent Application No. 2009313507, mailed on Nov. 17, 2014, 2 pages.
Notice Of Allowance received for Japanese Patent Application No. 2015-520522, mailed on Feb. 23, 2017. 3 pages of Official Copy Only.
Notice of Allowance received for Canadian Patent Application No. 2,727,429, mailed on May 26, 2015, 1 page.
Notice of Allowance received for Canadian Patent Application No. 2,779,600, mailed on Jul. 7, 2017, 1 page.
Notice of Allowance received for Chinese Patent Application No. 201380033808.3, mailed on Dec. 29, 2016, 4 pages (Official Copy Only).
Notice of Allowance received for Chinese Patent Application No. 201380041656.1, mailed on Mar. 3, 2017, 4 pages (Official Copy Only).
Notice of Allowance received for Japanese Patent Application No. 2015-036444, mailed on Jan. 13, 2017, 3 pages (Official Copy Only).
Notice of Allowance received for U.S. Appl. No. 15/652,070, mailed on May 21, 2019, 8 pages.
Notice of Allowance received for U.S. Appl. No. 14/515,130, mailed on May 2, 2016, 8 pages.
Notice of Allowance received for U.S. Appl. No. 14/515,130, mailed on May 25, 2016, 3 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Notice of Allowance received for U.S. Appl. No. 12/611,997, mailed on Apr. 15, 2015, 7 pages.
Notice of Allowance received for U.S. Appl. No. 13/207,381, mailed on Apr. 14, 2015, 7 pages.
Notice of Allowance received for U.S. Appl. No. 13/465,264, mailed on May 8, 2015, 7 pages.
Notice of Allowance received for U.S. Appl. No. 13/957,276, mailed on Aug. 28, 2015, 9 pages.
Notice of Allowance received for U.S. Appl. No. 14/271,276, mailed on Feb. 25, 2015, 8 pages.
Notice of Allowance received for U.S. Appl. No. 12/482,995, mailed on Dec. 24, 2014, 6 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Notice of Allowance received for U.S. Appl. No. 13/534,658, mailed on Jan. 5, 2017, 6 pages.
Notice of Allowance received for U.S. Appl. No. 13/534,658, mailed on Jan. 18, 2017, 4 pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.

(56) References Cited

OTHER PUBLICATIONS

Notice of Allowance received for U.S. Appl. No. 13/831,543, mailed on Oct. 8, 2014, 14 pages.
Notice of Allowance received for U.S. Appl. No. 14/061,554, mailed on Apr. 25, 2014, 8 pages.
Notice of Allowance received for U.S. Appl. No. 14/079,463, mailed on Apr. 1, 2014, 5 pages.
Notice of Allowance received for U.S. Appl. No. 14/218,858, mailed on Aug. 26, 2016, 8 pages.
Notice of Allowance received for U.S. Appl. No. 14/271,342, mailed on Mar. 13, 2015, 5 pages.
Notice of Allowance received for U.S. Appl. No. 14/273,063, mailed on Apr. 12, 2017. 7 pages.
Notice of Allowance received for U.S. Appl. No. 14/660,539, mailed on Apr. 6, 2018, 7 pages.
Notice of Allowance received for U.S. Appl. No. 14/693,155, mailed on Apr. 26, 2016, 9 pages.
Notice of Allowance received for U.S. Appl. No. 15/474,885, mailed on Feb. 14, 2018, 5 pages.
Notice of Allowance received for U.S. Appl. No. 13/615,107, mailed on Dec. 31, 2015, 10 pages.
Notice of Allowance received for U.S. Appl. No. 17/025,866, mailed on Jun. 23, 2022, 8 pages.
Notice of Allowance received for U.S. Appl. No. 17/025,866, mailed on Jul. 7, 2022, 3 pages.
Notice of Allowance received for U.S. Appl. No. 16/436,186, mailed on Apr. 22, 2022, 8 pages.
Notice of Allowance received for U.S. Appl. No. 16/436,186, mailed on Nov. 2, 2022, 7 pages.
Notice of Allowance received for U.S. Appl. No. 16/436,186, mailed on Nov. 10, 2022, 4 pages.
Office Action received for Australian Patent Application No. 2009257368, issued on Apr. 28, 2014, 4 pages.
Office Action received for Australian Patent Application No. 2009257368, issued on Jul. 31, 2013, 4 pages.
Office Action received for Australian Patent Application No. 2009313507, mailed on Nov. 13, 2013, 3 pages.
Office Action received for Australian Patent Application No. 2013284490, mailed on Jun. 5, 2017, 4 pages.
Office Action received for Australian Patent Application No. 2013300176, mailed on Nov. 10, 2016, 2 pages.
Office Action received for Canadian Patent Application No. 2,727,429, mailed on Apr. 14, 2015, 4 pages.
Office Action received for Canadian Patent Application No. 2,779,600, mailed on Jan. 4, 2016, 6 pages.
Office Action received for Canadian Patent Application No. 2,779,600, mailed on Oct. 19, 2016, 3 pages.
Office Action received for Chinese Patent Application No. 200980153687.X, mailed on Dec. 26, 2012, 11 pages of Official copy only.
Office Action received for Chinese Patent Application No. 200980153687.X, mailed on Jul. 11, 2013, 11 pages (Official copy only).
Office Action received for Chinese Patent Application No. 201380033808.3, mailed on Jul. 5, 2016, 9 pages (3 pages of English translation and 6 pages of Official copy).
Office Action received for Chinese Patent Application No. 201380041656.1, mailed on Jul. 5, 2016, 9 pages (4 pages of English translation and 5 pages of Official copy).
Office Action received for Chinese Patent Application No. 201380042887.4, mailed on Aug. 8, 2016, 9 pages (4 pages of English translation and 5 pages of Official copy).
Office Action received for European Patent Application No. 09763640.1, mailed on Dec. 2, 2016, 4 pages.
Office Action received for Japanese Patent Application No. 2011-513694, mailed on Aug. 27, 2013, 6 pages (3 pages of English Translation and 3 pages of Official copy).
Office Action Received for Japanese Patent Application No. 2011-513694, mailed on Jun. 10, 2014, 4 pages total (2 pages of Official Copy and 2 pages of English Translation) .
Office Action Received for Japanese Patent Application No. 2011-534914, mailed on Jan. 13, 2015, 9 pages (7 pages of English Translation and 2 pages of Official Copy.
Office Action Received for Japanese Patent Application No. 2011-534914, mailed on Jul. 15, 2014, 3 pages (1 page of English Translation and 2 pages of Official Copy).
Office Action received for Japanese Patent Application No. 2011-534914, mailed on May 10, 2016, 10 pages ( 4 pages of Official Copy and 6 pages of English Translation).
Office Action received for Japanese Patent Application No. 2011-534914, mailed on Oct. 1, 2013, 5 pages (2 pages of English Translation and 3 pages of Official copy).
Office Action received for Japanese Patent Application No. 2014-158517, mailed on Feb. 15, 2017, 8 pages (5 pages of English Translation and 3 pages of Official Copy Only).
Office Action Received for Japanese Patent Application No. 2014-158517, mailed on Jun. 22, 2017. 14 pages of official Copy only.
Office Action Received for Japanese Patent Application No. 2014-158517, mailed on May 19, 2015, 5 pages (2 pages of English Translation and 3 pages of Official Copy).
Office Action received for Japanese Patent Application No. 2015-036444, mailed on Feb. 23, 2016, 3 pages of English translation only.
Office Action received for Japanese Patent Application No. 2015-526523, mailed on Jan. 25, 2017, 8 pages (5 pages of English Translation and 3 pages of Official Copy Only).
Office Action received for Japanese Patent Application No. 2016-143049, mailed on Apr. 24, 2017. 5 pages (2 pages of English Translation and 3 pages of Official copy).
Office Action received for Japanese Patent Application No. 2015-036444, mailed on Sep. 14, 2016, 5 pages (3 Pages of English Translation and 2 Pages of Official Copy).
Office Action received for Japanese Patent Application No. 2016-094326, mailed on Dec. 2, 2016, 4 pages (2 pages of English Translation and 2 pages Official Copy Only).
Office Action received for Japanese Patent Application No. 2016-094326, mailed on Jul. 6, 2017, 2 pages (Official Copy Only).
Rosenschein et al., (1992). "Shock-Wave Thrombus Ablation, a New Method for Noninvasive Mechanical Thrombolysis," The American Journal of Cardiology, 70:1358-1361.
Sakes et al., (2016). "Crossing Total Occlusions: Navigating Towards Recanalization," Cardiovascular Engineering and Technology, 7(2):103-117.
Third Party Preissuance Submission for U.S. Appl. No. 16/436,186, filed Jan. 10, 2020, 3 pages.
Written Opinion received for PCT Patent Application No. PCT/US2012/023172, mailed on Sep. 28, 2012, 4 pages.
Written Opinion received for PCT Patent Application No. PCT/US2009/047070, mailed on Jan. 19, 2010, 5 pages.
Zhong et al., (1997). "Transient Oscillation of Cavitation Bubbles Near Stone Surface During Electrohydraulic Lithotripsy," Journal of Endourology, 11(1):55-61.
Examiner Interview Summary Record received for U.S. Appl. No. 17/477,483, mailed on Oct. 2, 2023, 3 pages.
Notice of Acceptance received for Australian Patent Application No. 2019290401, mailed on Feb. 14, 2025, 3 pages.
Notice of Allowance and Examiner Interview Summary Record received for U.S. Appl. No. 17/477,483, mailed on Jan. 22, 2024, 10 pages.
Notice of Allowance and Examiner Interview Summary Record received for U.S. Appl. No. 18/104,170, mailed on Aug. 14, 2024, 8 pages.
Notice of Allowance and Search Report received for Chinese Patent Application No. 202080081128.9, mailed on Oct. 15, 2024, 6 pages. English translation.
Notice of Allowance received for Australian Patent Application No. 2020354380, mailed on Mar. 3, 2026, 3 pages.
Notice of Allowance received for Australian Patent Application No. 2021371050, issued on Jan. 22, 2026, 3 pages.
Notice of Allowance received for Chinese Patent Application No. 201980041113.7, mailed on Oct. 28, 2024, 7 pages. English translation.

(56) References Cited

OTHER PUBLICATIONS

Notice of Allowance received for Japanese Patent Application No. 2024-096585, mailed on Mar. 2, 2026, 4 pages. English translation.
Notice of Allowance received for U.S. Appl. No. 17/477,483, mailed on Feb. 1, 2024, 2 pages.
Notice of Allowance received for U.S. Appl. No. 17/477,483, mailed on Feb. 9, 2024, 2 pages.
Notice of Allowance received for U.S. Appl. No. 17/477,483, mailed on Mar. 6, 2024, 2 pages.
Notice of Allowance received for U.S. Appl. No. 18/104,170, mailed on Sep. 5, 2024, 4 pages.
Office Action received for Australian Patent Application No. 2020354380, mailed on May 19, 2025, 5 pages.
Office Action received for European Patent Application No. 21805823.8, mailed on Feb. 7, 2025, 4 pages.
Office Action received for Japanese Patent Application No. 2023-524897, mailed on May 13, 2025, 8 pages. English translation.
Office Action received for Mexican Patent Application No. MX/a/2023/004878, mailed on Oct. 31, 2025, 7 pages. English translation.
Office Action received for U.S. Appl. No. 17/477,483, mailed on Jun. 22, 2023, 22 pages.
Office Action received for U.S. Appl. No. 17/948,528, mailed on Jan. 8, 2025, 19 pages.
Office Action received for U.S. Appl. No. 18/104,170, mailed on Apr. 24, 2024, 9 pages.
Requirement for Restriction received for U.S. Appl. No. 18/104,170, mailed on Feb. 28, 2024, 5 pages.

* cited by examiner 100
112
110
108
106
104
A
102

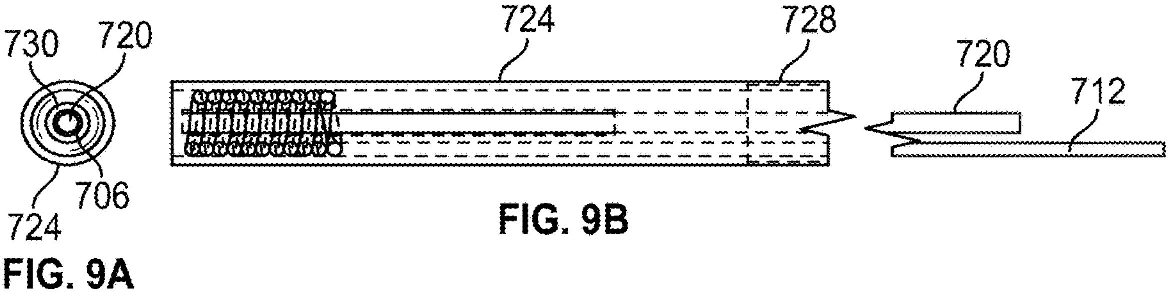
FIG. 9A
FIG. 9B
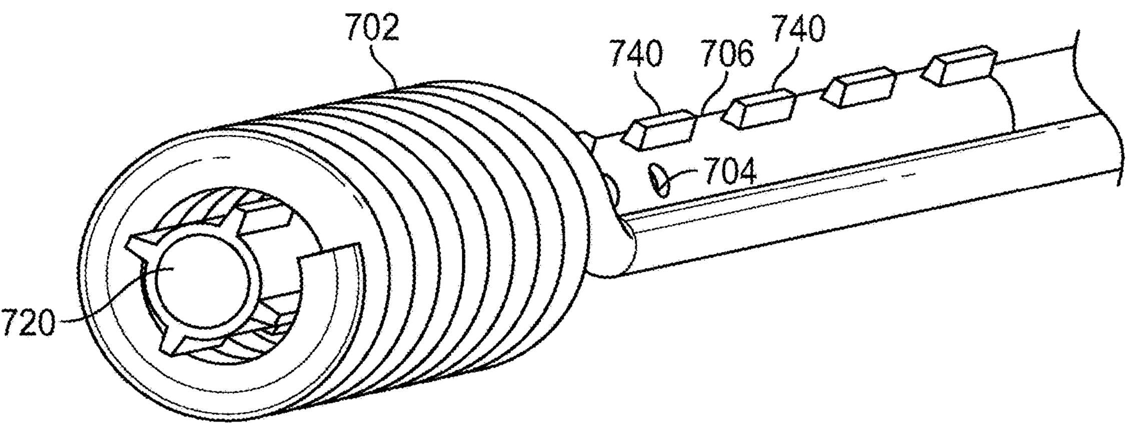
FIG. 10

SYSTEM FOR TREATING OCCLUSIONS IN BODY LUMENS

PRIORITY

This application is a divisional of U.S. patent application Ser. No. 18/104,170, filed Jan. 31, 2023, which is a divisional of U.S. patent application Ser. No. 16/436,186, filed Jun. 10, 2019, now U.S. Pat. No. 11,596,423, which claims priority to U.S. Patent Application Ser. No. 62/688,110 filed Jun. 21, 2018, the entire disclosure of each of which is incorporated herein by reference.

BACKGROUND

The present disclosure relates generally to a system for treating occlusions in a body lumen. The system is useful for a chronic total coronary occlusion ("CTO"), a partial coronary occlusion, or a kidney stone in ureter, in order to restore normal flow in a lumen (e.g., the artery or the ureter).

In angioplasty or peripheral angioplasty procedures, an angioplasty balloon is used to dilate a lesion (e.g., calcified lesion) and restore normal blood flow in the artery. In some examples, an angioplasty balloon is advanced into the vasculature (e.g., along a guide wire) until the balloon is aligned with calcified plaques. The balloon is then pressurized with a fluid to expand the vessel to permit blood flow.

More recently, a system has been developed wherein electrodes are disposed in the angioplasty balloon. Once the balloon is initially positioned adjacent a blockage, a series of high voltage pulses are applied to the electrodes in a manner to generate a series of shock waves. The shock waves act to crack calcified lesions. Once the lesions are cracked, the balloon can be inflated, in a more gentle fashion, to expand the vessel and improve circulation.

Further information about the latter type of device can be found in U.S. Pat. Nos. 8,856,371; 8,747,416 and 9,642,673. Shock wave technology has also been developed for treating heart valves (U.S. 2018/0098779) and for guide wire designs (U.S. Pat. No. 9,730,715). U.S. Patent Publication 2018/03640482 describes a forward directed shock wave device. Each of these patent documents is incorporated herein by reference.

Arteries are sometimes totally or partially occluded, for example, with thrombus, plaque, fibrous plaque, and/or calcium deposits. When this condition is present, the physician must first cross the occlusion, and then feed the angioplasty balloon and/or other tools down the artery to the desired location of blockage to perform the desired procedure. However, in some instances (e.g., CTO), the occlusion is so tight and solid, making it difficult to cross the treatment device into the true lumen of the distal vessel.

CTOs remain a challenge in percutaneous coronary interventions, as well as a challenge for the periphery, causing critical limb ischemia and amputations. First, many of the currently available equipment are incapable of physically crossing the tough proximal cap or distal cap (retrograde approach) of the CTO. In some instances, attempting to penetrate the CTO cap using soft guide wire causes buckling (e.g., deflecting the guidewire to a subintimal passage or collateral branch). On the other hand, stiffer guide wires may damage the artery wall when forced against the CTO. Moreover, some currently available equipment operate by generating strong mechanical vibrations to break the CTO, but the intensity of the vibration may damage the artery wall and make the system less durable and more difficult to control.

Similar issues are present for occlusions formed in other parts of the body, for example, kidney stones in a ureter.

BRIEF SUMMARY

The invention provides a system for treating an occlusion such as CTO or kidney stones within a lumen such as a blood vessel or a ureter. In some embodiments, the system comprises an insulated outer sheath, an elongated conductive tube, wherein the insulated outer sheath is circumferentially mounted around the elongated conductive tube, and an insulated wire having a helically coiled portion at a distal end of the insulated wire. The coiled portion includes an exposed distal tip. A distal portion of the elongated conductive tube is circumferentially mounted around the distal coiled portion of the insulated wire. When a voltage is applied across the insulated wire and the elongated conductive tube, a current is configured to flow from the exposed distal tip of the insulated wire to the elongated conductive tube to ionize the fluid around it and generate a plurality of cavitation bubbles and bubble-associated dynamics (collapses, jets, etc.).

In some embodiments, a method for treating an occlusion within a lumen such as a blood vessel or a ureter comprises advancing a treatment device within the lumen to contact the occlusion. The treatment device comprises: an insulated outer sheath; an elongated conductive tube, wherein the insulated outer sheath is circumferentially mounted around the elongated conductive tube; and an insulated wire having a helically coiled portion at a distal end of the insulated wire, wherein the coiled portion includes an exposed distal tip and wherein a distal portion of the elongated conductive tube is circumferentially mounted around the distal coiled portion of the insulated wire. The method further comprises injecting conductive fluid (i.e. physiological saline, mixture of saline and angiographic contrast dyes, etc.) toward a distal end of the treatment device; and applying a voltage across the insulated wire and the elongated conductive tube to cause a current to flow from the exposed distal tip of the insulated wire to the elongated conductive tube to generate a plurality of cavitation bubbles and bubble-associated dynamics (collapses, jets, etc.).

In some embodiments, a system for treating an occlusion within a body lumen is disclosed. The system includes an insulated wire having a helically coiled portion near the distal end thereof, and with the distal tip of the insulated wire having a portion of the insulation removed to define an electrode. The system further includes an elongated central electrode with the distal end thereof being received within the helically coiled portion of the insulated wire. In one preferred embodiment, the system further includes an insulated tube located about the distal end of the central electrode and within the helically coiled portion of the insulated wire. Finally, a tubular outer shell is provided for covering the coiled portion of the insulated wire. The proximal ends of the insulated wire and the central electrode are connectable to the terminals of an electrical pulse generator so that in use, when voltage pulses are applied to the central electrode and the insulated wire, a series of cavitation bubbles are created between the electrode of the insulated wire and the central electrode.

DESCRIPTION OF THE FIGURES

FIG. 9A is an end view of the system of FIG. 7.

FIG. 9B is a cross-sectional view of the system of FIG. 7.

FIG. 10 is a perspective view of a bubble generating tip system of another exemplary in accordance with some embodiments.

DETAILED DESCRIPTION

The following description sets forth exemplary methods, parameters, and the like. It should be recognized, however, that such description is not intended as a limitation on the scope of the present disclosure but is instead provided as a description of exemplary embodiments.

Described herein are exemplary systems and methods for treating an occlusion such as CTO or kidney stones in a ureter. In according with some embodiments, the treatment system includes a forward bubble generating tip to be advanced within the lumen to contact the occlusion. The forward bubble generating tip includes electrodes that, when provided with a relatively low-voltage and high-PRF (pulse repetition rate) generator, form plasma arcs that in turn lead to cavitation bubbles. The cavitation bubbles create mechanical vibrations, turbulence, jets, and/or forceful collapses to break the occlusion. The output of the generator is configured to be sufficient for creating electro-hydraulic discharge and cavitation bubbles for effectively drilling, but not enough to create a powerful shock wave that may compromise the durability of the system. As such, the mechanical vibrations are relatively gentle compared to currently available equipment. Accordingly, the treatment system is less likely to cause damage to the lumen wall (e.g., vessel wall) and is easier to control and more durable.

Figure 1:
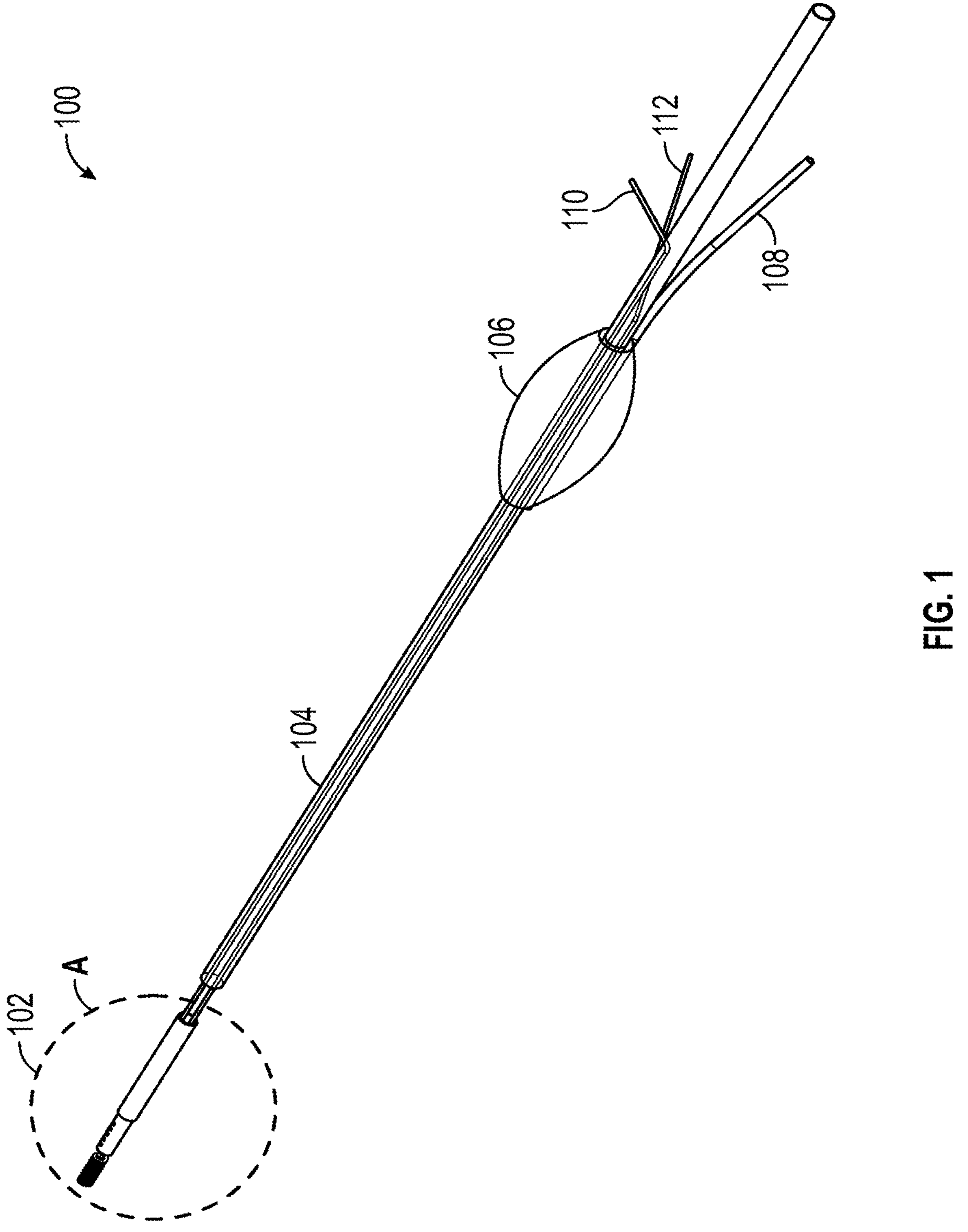
FIG. 1 is a perspective view of an exemplary system for treating an occlusion, in accordance with some embodiments.

FIG. 1 is a perspective view of an exemplary treatment system 100 in accordance with some embodiments. The treatment system includes a forward bubble generating tip 102 (shown in an expanded view), an insulated outer sheath 104, a proximal balloon 106 mounted over a length of the insulated outer sheath, a waste conduit 108, and insulated wires 110 and 112. The forward bubble generating tip 102 includes electrodes and is described in detail with reference to FIGS. 2A-C. In operation, conductive fluid such as saline (or saline contrast mix) is injected from the proximal opening of the insulated outer sheath 104 and flows toward the distal end. When the proximal ends of the insulated wires 110 and 112 are connected to a voltage supply, cavitation bubbles and/or shock waves are generated via the conductive fluid at the forward bubble generating tip. The cavitation bubbles and/or shock waves lead to sustained mechanical vibrations in the forward direction, breaking down the occlusion such as CTO or kidney stones. As more conductive fluid is injected, debris such as broken down occlusion pieces, metals, and bubbles are flushed toward the proximal balloon and carried out of the lumen via the waste conduit 108.

Figure 2A:
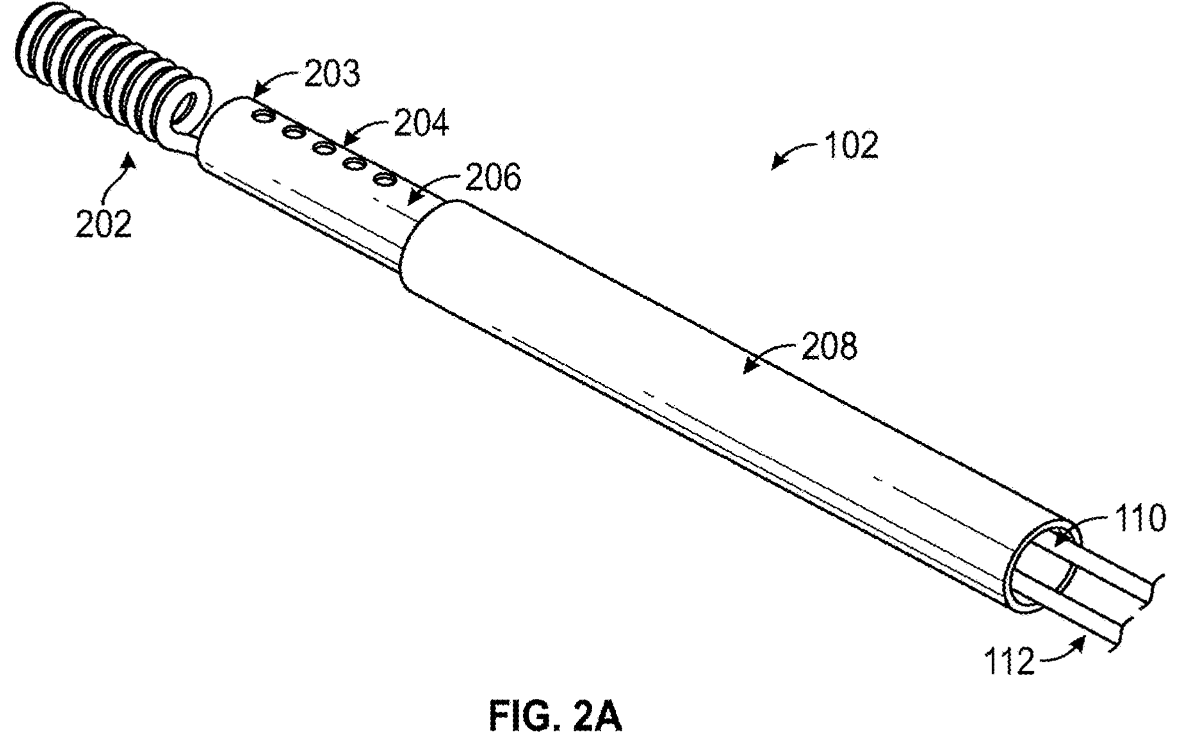
FIG. 2A is an expanded view of an exemplary bubble generating tip of the treatment system, in accordance with some embodiments.

FIG. 2A depicts an expanded view of the forward bubble generating tip 102 of FIG. 1. As depicted, the forward bubble generating tip 102 includes an elongated conductive tube 208, a helically coiled portion 202 at the distal end of the insulated wire 112, and an optional insulated layer 206 disposed between the elongated conductive tube 208 and the helically coiled portion 202. In the depicted example, the insulated layer 206 includes a plurality of holes 204 arranged along the longitudinal axis. In some examples, the elongated conductive tube 208 can be a stainless steel hypotube. The insulated wires 110 and 112 can be polyimide-insulated copper wires. The insulated layer 206 can be a polyimide tubular insulator. The insulated layer provides an extra layer of insulation between the conductive core of wire 112 and the elongated conductive tube 208 and is helpful in case the insulation around the coiled portion 202 has defects and/or experiences damages (e.g., scratching during assembly). In some examples, the forward bubble generating tip 102 does not include the insulated layer 206. In some examples, epoxy or cyano glue can be used between the coiled portion 202 and the elongated conductive tube 208 to fix the relative positioning of the two.

Figure 2B:
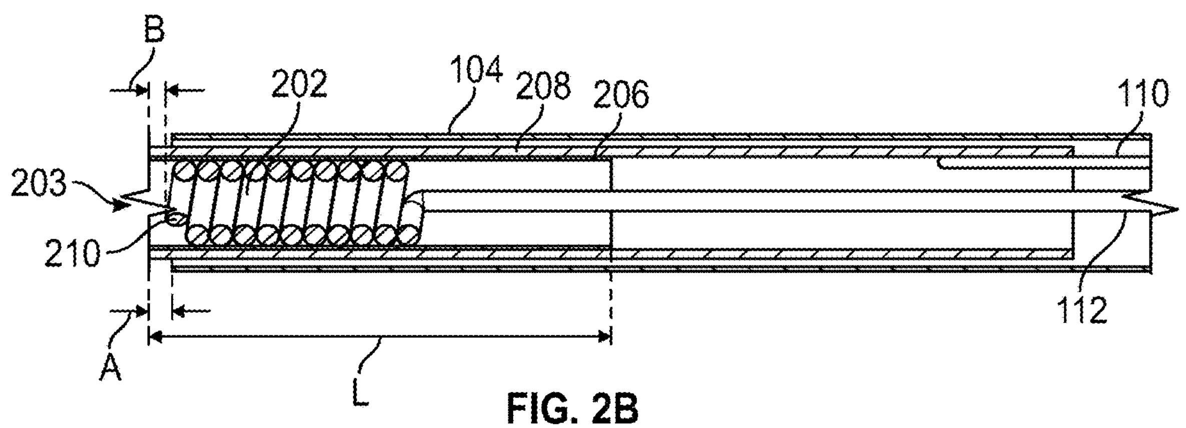
FIG. 2B is a cross-sectional view of an exemplary bubble generating tip of the treatment system, in accordance with some embodiments.

FIG. 2B depicts a cross-sectional view of the forward bubble generating tip 102. As depicted, the insulated outer sheath 104 is circumferentially mounted over the elongated conductive tube 208. In the depicted example, the distal edge of the elongated conductive tube 208 extends over distal edge of the insulated outer sheath 104 by distance A. The distance A can be adjusted based on the characteristics of the occlusion. For example, the distance A can be set to be longer than the thickness of the calcified cap of the CTO to be drilled through. If not, the crossing profile would need to be undesirably increased (i.e. a bigger hole needs to be drilled to accommodate the insulated outer sheath). In some examples, the distance A ranges from 0.004" to 0.01". As further depicted, an insulated layer 206 is disposed, for a longitudinal length of L, between the elongated conductive tube 208 and the helically coiled wire portion 202. The distal end of the insulated wire 110 is welded to the elongated conductive tube 208.

As depicted, the distal edge of the insulated layer 206 is aligned with the distal edge of the elongated conductive tube 208. Further, the distal edge of the elongated conductive tube 208 extends beyond the helically coiled wire portion 202 by distance B. In some examples, the distance B ranges from 0 mm (i.e., the distal end of the coiled portion is aligned with the distal edge of the elongated tube) to 0.5 mm. In some examples, one or more of the other factors that affect the efficiency of the operation, such as the flow rate of the conductive fluid, the applied voltage, the shape and composition of the occlusion, are taken into account when setting distance B to achieve an optimal configuration. This relative positioning of the helically coiled wire portion 202 and the distal edges of the insulated layer 206 and elongated conductive tube 208 ensures safety to the surrounding tissue, protects the catheter from the vibrations emitting from the tip, and causes the mechanical vibrations to be generated in a forward-facing direction, thus increasing the intensity, and thus the effectiveness, of the treatment system in breaking down the occlusion. Further, the forward-facing mechanical vibrations, along with the continuous flow rate in the forward direction, result in drilling of holes that are consistent (e.g., in size, in shape), thus making the treatment system easier to operate. In some examples, the treatment system is configured to drill holes of around 1 mm in diameter in calcified materials.

In some examples, the flow of saline or saline/angiographic contrast mix is adjusted to avoid over-heating issues and control drilling efficiency and rate. In some examples, the flow rate is configured to be in the range of 1 to 30 mL/min to improve breakability of calcified structures.

In an exemplary operation, when the proximal ends of the insulated wires 110 and 112 are connected to the negative port and positive port of a generator, respectively, a current flows from the distal end 210 of the insulated wire 112 to the elongated conductive tube 208. The current can cause a plurality of plasma arcs to be formed between the distal end 210 of the insulated wire 112 and the inner diameter of the elongated conductive tube 208 (e.g., across the distal edge 203 of the insulated layer 206 or through the holes 204 in 206). The plasma arcs lead to cavitation bubbles in a controlled fashion (one at a time, at a particular rate), which in turn lead to mechanical vibrations, and other bubble dynamics-related effects such as collapses, turbulence, jetting, etc. in the conductive fluid (e.g., via the expansion and collapse of the bubbles). The mechanical vibrations serve to break or chip away the occlusion. As compared to the generators used in the prior art shock wave generation systems mentioned above, the generator for this system is configured to generate lower-voltage pulses at a higher pulse repetition rate in order to minimize the strength of the shock waves and optimize and maximize bubble growth and collapse. For example, in the prior art systems, each pulse might be about 3000 volts with a 1 Hz repetition rate. In this system, the voltage can be under 1000 volts with the repetition rates ranging from 14 to 200 Hz. In a preferred embodiment, repetition rates can as high as 800 Hz.

As the plasma arcs cause erosion to the electrodes in operation, the helically coiled wire portion 202 and/or the insulation over the coiled wire portion can disintegrate and shorten over time. Similarly, the insulation layer 206 and the distal edge of the elongated conductive tube 208 can disintegrate due to use. The rates at which the coiled wire portion, the insulated layer, and the elongated conductive tube disintegrate can vary based on physical characteristics of each component (e.g., the diameter of the wire, the property of the wire, the thickness of the insulation layer), the polarities of the applied voltage, the magnitude of the applied voltage, etc. For example, a wire that is relatively thin, connected to a relatively high voltage supply, and/or connected to the positive voltage port would erode faster. In some instances, before the helically coiled wire portion 202 experiences extensive usage, the plasma arcs are generated across the distal edge 203 of the insulated layer 206. However, as the helically coiled wire portion 202 shortens due to usage, the distance between the distal end 210 of the insulated wire 112 and the distal edge of the insulated layer 206 increases. Due to the increased distance, plasma arcs are no longer generated across the distal edge 203 of the insulated layer 206. Instead, as current flows from the distal end 210 of the helically coiled wire portion 202 to inner diameter of the elongated conductive tube 208, plasma arcs are generated across one of the holes 204 (e.g., the hole located closest to the distal end 210 of the shortened helically coiled wire portion) in the insulated layer 206. As shown in FIG. 2A, a plurality of holes are provided along the longitudinal axis of the insulated layer 206, thus allowing plasma arcs to be formed even as the helically coiled wire portion 202 shortens and improving the durability of the treatment system. In other words, the holes in the conductive layer aim to become new spark areas as the device (i.e., the electrodes) erodes. In some examples, the plurality of holes is arranged in a spiral orientation to be aligned with the coil to control the maximum arc length. In some examples, the applied voltage is sustained for a relatively long periods of time (e.g., minutes) to achieve continuous generation of cavitation bubbles and eventual crossing. Note that as the coiled wire portion erodes, the location of the generation of the cavitation bubbles will change. In the illustrated embodiment, the location of the generation of the cavity bubbles will rotate circumferentially about the periphery of the conductive tube 208.

In some examples, various parameters can be adjusted during the operation to slow down or even out the erosion of the electrodes. For example, the frequency of bubble generation/emission (pulses per minute) can be adjusted to control the tip erosion, durability and drilling time. The frequency of bubble generation can be controlled by reducing the capacitance (so a capacitance switch can change the speed on demand), or by reducing the current power supply. As another example, the applied voltage can be adjusted as a function of drilling time to control the emitter erosion and device durability while maintaining the frequency constant as a function of drilling time. Further, polarity of the electrodes can be reversed for a period of time equivalent to a fraction of the treatment time (e.g., 10% to 100% of the time) while maintaining the voltage and frequency constant as a function of drilling time in order to control electrode wear and improve device durability. Further still, the thickness of the wire insulation can be chosen to control the durability of the wire.

U.S. Pat. No. 10,226,265, incorporated by reference, teaches various approaches for switching polarity of electrode pairs positioned in a conductive fluid. Those types of approaches can be utilized with the subject device. In particular, to maintain peak sonic output, the spark gap should be constant. As the electrodes erode away, the gap can vary. To compensate for this variation in gap size, the polarity on the electrodes can be reversed. The polarity reversal frequency can be used to help control variations in the length of the spark gap. It is possible to tune the polarity reversal frequency based on the power being delivered, wire diameter and insulator thickness. It is also possible to have the generator detect the power degradation and automatically reverse the polarity on the electrodes.

Figure 2C:
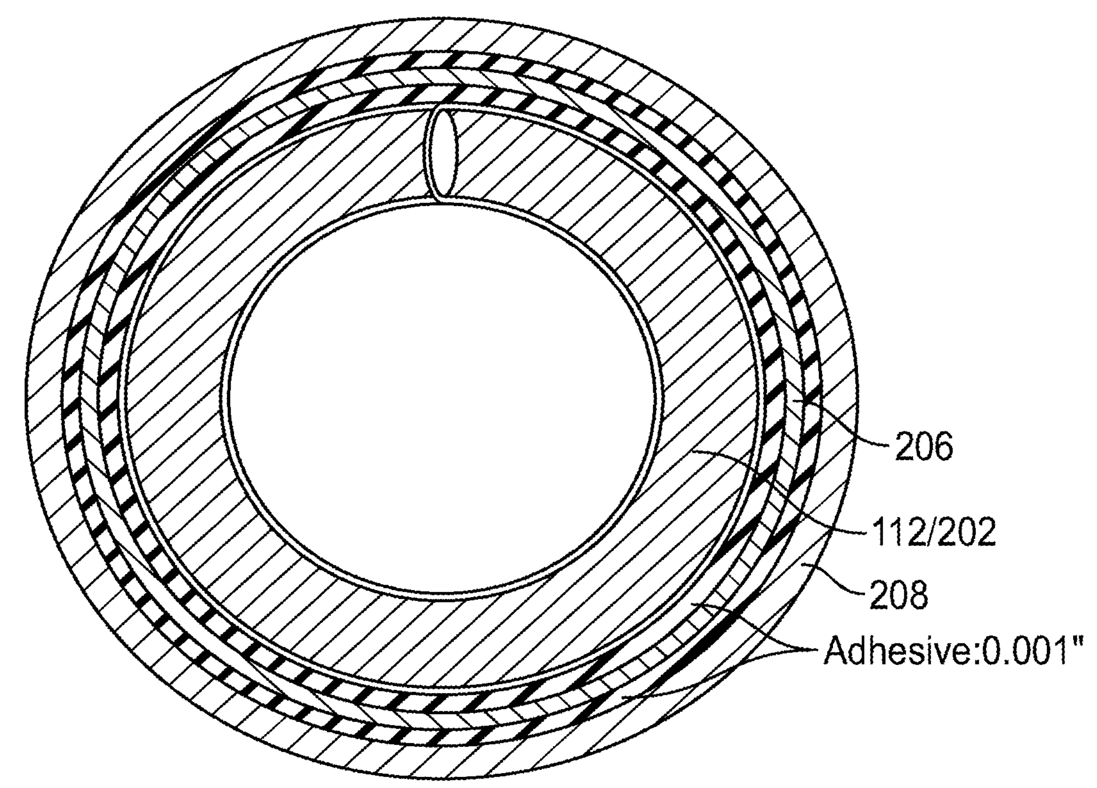
FIG. 2C is a cross-sectional view of an exemplary bubble generating tip of the treatment system, in accordance with some embodiments.

FIG. 2C is a cross-sectional view of an exemplary bubble generating tip of the treatment system, in accordance with some embodiments. The insulated wire 112 has a typical diameter of 0.005" in the core (e.g., copper core) with 0.0005" polyimide coating. The number of turns of the coiled wire portion dictates the life of the electrode. With ~500V-700V arcing at 100 Hz, one turn can last approximately 30-40 seconds. Thus, for a 10-minute procedure, the coiled wire portion can include around 17 turns and the coil length would be around 0.1". The length of the elongated conductive tube 208 should be longer than the coil length to support internal features. The insulated layer 206 (e.g., polyimide insulator sheath) can have a thickness of 0.001". The outer diameter of the insulated layer 206 is fitted inside the inner diameter of the elongated conductive tube 208. The outer diameter of the elongated conductive tube 208 (e.g., stainless steel hypotube) can range between 0.035" to 0.065" with the thickness of 0.002". Arcing gap between the wire core (e.g., copper core) and the inner diameter of the elongated conductive tube is around 0.004"-0.007". The arc gap could be longer if the insulting layer 206 and a hole 204 is further away, for example the other side of the tube. In some examples, the arcing gap is the ideal range to maximize the cavitation. In some examples, the various dimensions of the system are selected to be compatible with off-shelf components.

Figure 3:
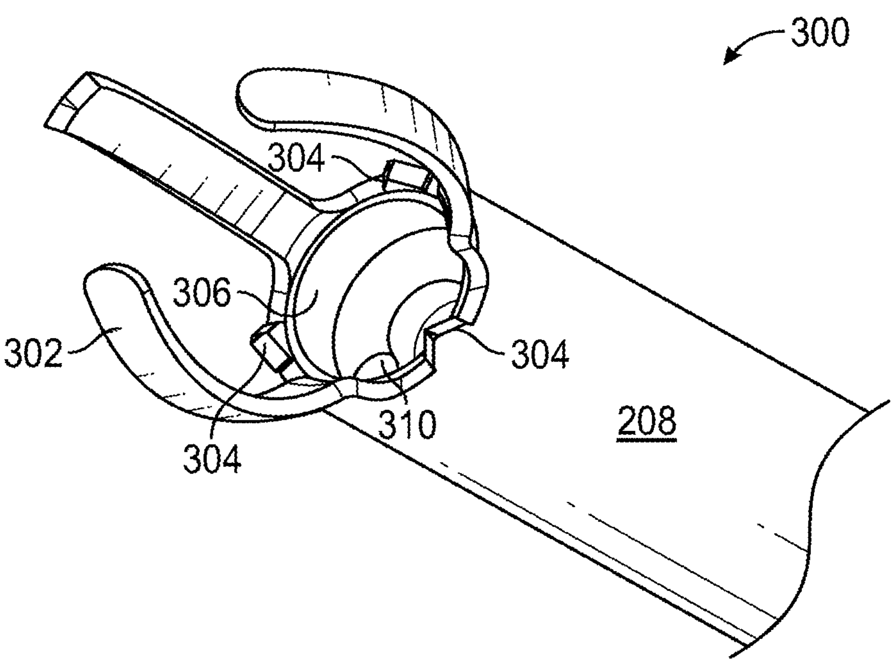
FIG. 3 is a perspective view of another exemplary bubble generating tip of the treatment system, in accordance with some embodiments.

FIG. 3 depicts a perspective view of an alternative forward bubble generating tip 300 of the treatment system, in accordance with some embodiments. The forward bubble generating tip 300 includes a plurality of atraumatic arms or tines 302 extending from the distal end of the elongated conductive tube 208. The tines 302 are made of flexible materials and are designed to deflect the tip from perforating the lumen wall. In some examples, the tines can be coated with elastomer (i.e., silicone rubber) or low durometer polymer (i.e., polyurethane), and can be around 0.035" in length. When the forward bubble generating tip drills a hole through the occlusion and gets to soft tissue, the flexible tines cause the tip to turn. Further, the forward bubble generating tip 300 includes a plurality of spikes 304 extending from the distal end of the elongated conductive tube 208. The spikes 304 are designed to direct the plasma arcs between the distal end 310 of the coiled wire portion and the distal edge of the elongated conductive tube 208, for example, across the distal edge of the insulated layer 306.

Figure 4:
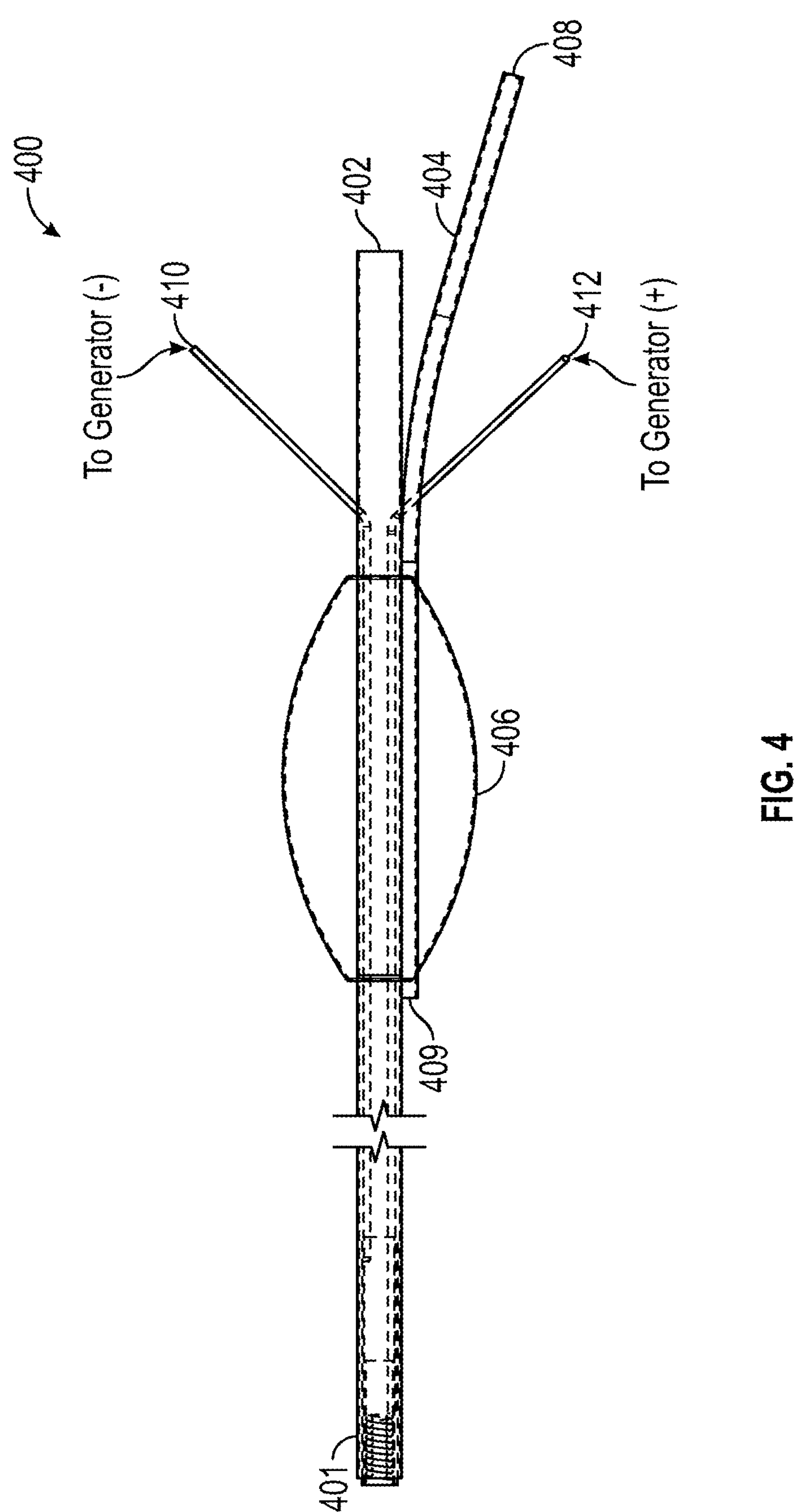
FIG. 4 is a side view of an exemplary system for treating an occlusion, in accordance with some embodiments.

FIG. 4 is a side view of an exemplary system 400 for treating an occlusion, in accordance with some embodiments. As depicted, the proximal end of the insulated outer sheath forms an inlet 402 for injecting conductive fluid (e.g., saline). This port 402 could also act as a conduit to introduce a guidewire (e.g., a 0.014" guidewire) after flushing or while flushing the saline. The injected conductive fluid serves a number of purposes. First, when the proximal ends of wires 410 and 412 are connected to a voltage supply, plasma arcs can be formed via the conductive fluid at the forward bubble generating tip, as described above with reference to FIGS. 1-3. Further, continually injecting conductive fluid helps to dissipate heat and cool the electrodes. Flow also creates forward inertia to help the bubbles to drill and collapse (and jet) forward. In some example, the flow rate is adjusted to control the drilling efficiency and rate. Moreover, the conductive fluid flushes through the coiled wire portion at the forward bubble generating tip and carries the debris such as broken down occlusion pieces, metals, and bubbles away from the forward bubble generating tip 401 toward the proximal balloon 406. The proximal balloon, when inflated, traps the debris and prevents the debris from entering the main artery. As depicted, a conduit 404 extends through the proximal balloon 406, and the distal end 409 of the conduit 404 serves as a waste inlet for receiving the flushed debris and transporting the debris to the waste outlet 408 at the proximal end of the conduit. In some examples, suction is provided at the proximal end of the conduit 404 to facilitate the removal of debris. The rapid removal of debris helps to refresh the cavitation.

Figure 5:
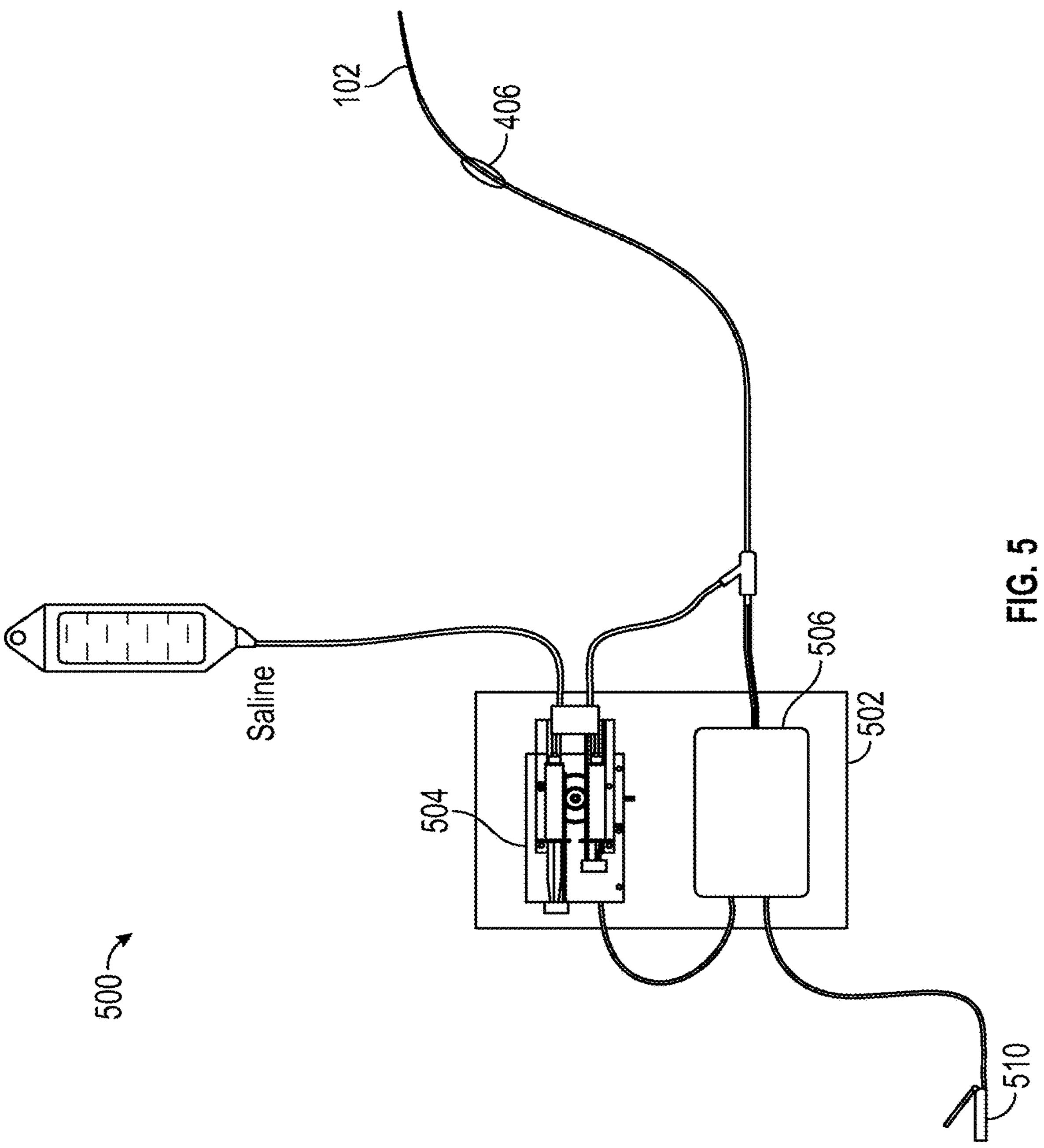
FIG. 5 is a schematic view of an exemplary system for treating an occlusion, in accordance with some embodiments.

FIG. 5 is a schematic view of an exemplary system 500 for treating an occlusion, illustrating further aspects of the invention. The system 500 further includes a control console 502 having an infusion pump 504 and a generator 506. The infusion pump provides the flow of conductive fluid (e.g., saline) toward the forward bubble generating tip via the irrigation lumen. In some examples, an auxiliary pump may be used for aspiration and removal of debris. The generator serves as a voltage supply for the electrodes at the forward bubble generating tip. The pulses have a voltage in the range of 500 to 3000 volts and more preferably 600 to 1000 volts. Ideal electrical energies applied for CTO crossing are very low (between 5 and 50 mJ per pulse) to avoid generating excess heat, and more preferably 30 mJ. Current ranges from 1-15 Amperes. The pulses are generated with a repetition rate in the range of 14 to 800 Hz. In some examples, the system further includes a visualization system and/or a steering system for properly navigating (e.g., side branches) and placing the forward bubble generating tip. Alternatively or additionally, the forward bubble generating tip could be made of a radiopaque material that is easy to see under fluoroscopic guidance. Thus, instead of steel, materials filled with Barium sulfate, tungsten or other radiopaque materials, or materials filled with radiopaque materials can be used so that the device can be tracked.

In use, a guidewire can be advanced through the central open region in the device and towards the hole drilled or being drilled in the occlusion. For example, the guidewire can be advanced through the drilled hole to guide the advancement of the treatment system, which continues drilling until the occlusion is crossed. In some examples, the guidewire can be advanced through the elongated conductive tube (e.g., from saline inlet 402), more specifically, through the center of the coiled portion of the bubble generating tip. After the occlusion is crossed, the forward bubble generating tip can be withdrawn, while the guidewire can remain to allow the access of other tools such as angioplasty or Lithoplasty™ balloons using over the wire entry. Lithoplasty is the trademark of assignee directed to its intravascular lithotripsy (shock wave) catheters. As discussed below, after the hole is drilled, an angioplasty balloon catheter can be advanced through the drilled hole to a distal end of the occlusion and aligned with the occlusion.

Figure 6:
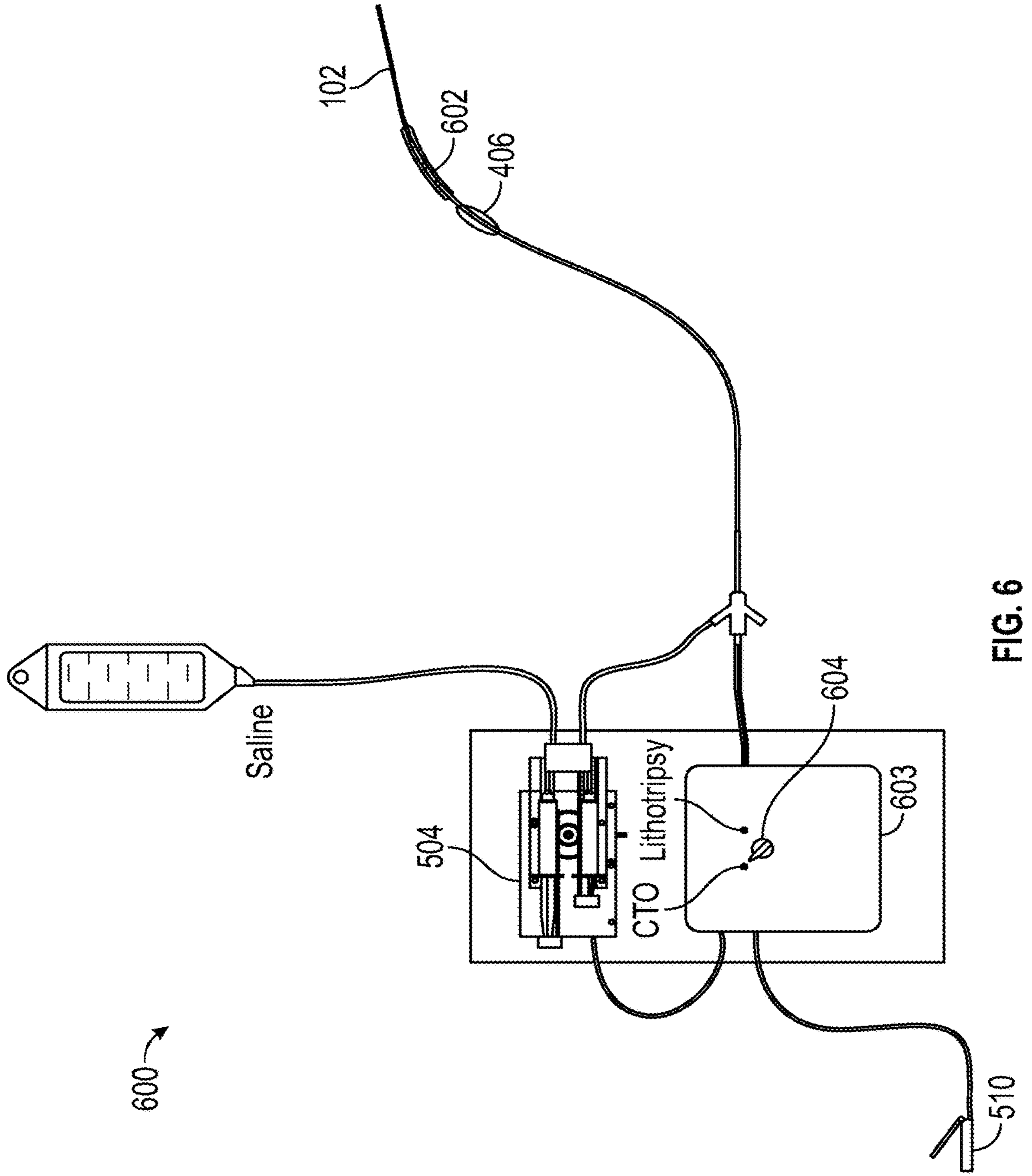
FIG. 6 is a schematic view of another exemplary system for treating an occlusion, in accordance with some embodiments.

FIG. 6 is a schematic view of another exemplary system 600 for treating an occlusion, in accordance with some embodiments. The treatment system can be used alone or in conjunction with an angioplasty balloon 602. In some examples, the forward bubble generating tip is first advanced within a lumen (e.g., blood vessel or ureter) to contact the occlusion to drill a hole through the occlusion in accordance with processes described above. Thereafter, the balloon is advanced to the lesion. The balloon 602 is then pressurized with a fluid to expand the lumen to enhance flow (e.g., blood flow). As noted above, the advancement and positioning of the balloon can be aided with a guidewire passed through the center of the device.

As an alternative, the angioplasty balloon is a lithotripsy balloon and a shock wave generator may be disposed within the balloon 602. The shock wave generator may take the form of, for example, a pair of electrodes. When the balloon 602 is aligned with the distal end of the occlusion and a high voltage pulse is applied across the electrodes, a shock wave is formed that propagates through the fluid and impinges upon the wall of the balloon and the occlusion. Repeated shock waves break up the occlusion without damaging surrounding soft tissues. In some examples, the shock waves can be generated along an axis perpendicular to the axis of the catheter (instead of being forwardly directed) so that they treat different parts of the occlusion. The angioplasty balloon 602 can then be expanded to further open up the lumen. As depicted in FIG. 6, the control console 603 includes a selector switch 604 for selecting between "CTO" and "Lithoplasty™" for switching the voltage supply between providing lower voltage pulses to the forward bubble generating tip and providing higher voltage pulses to the shock wave generator within the balloon 602. In this example, the proximal balloon can be placed on either side of the lithotripsy balloon.

Figure 7:
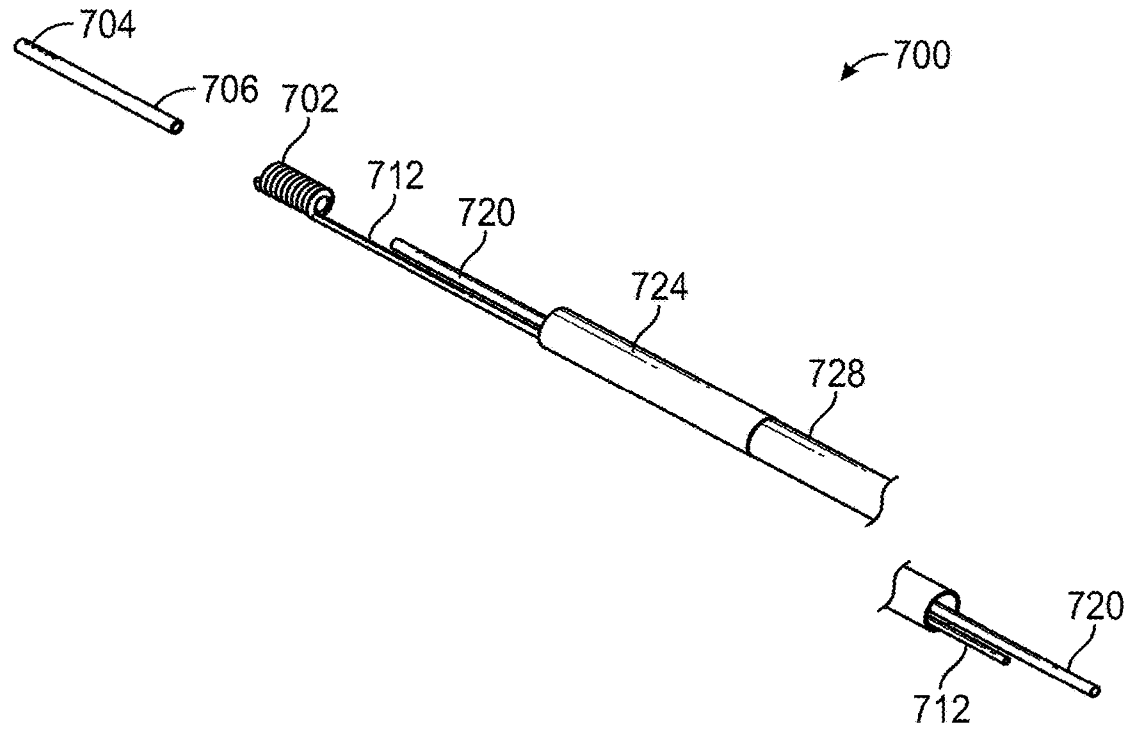
FIG. 7 is an expanded view of another exemplary system for treating an occlusion, in accordance with some embodiments.
Figure 8:
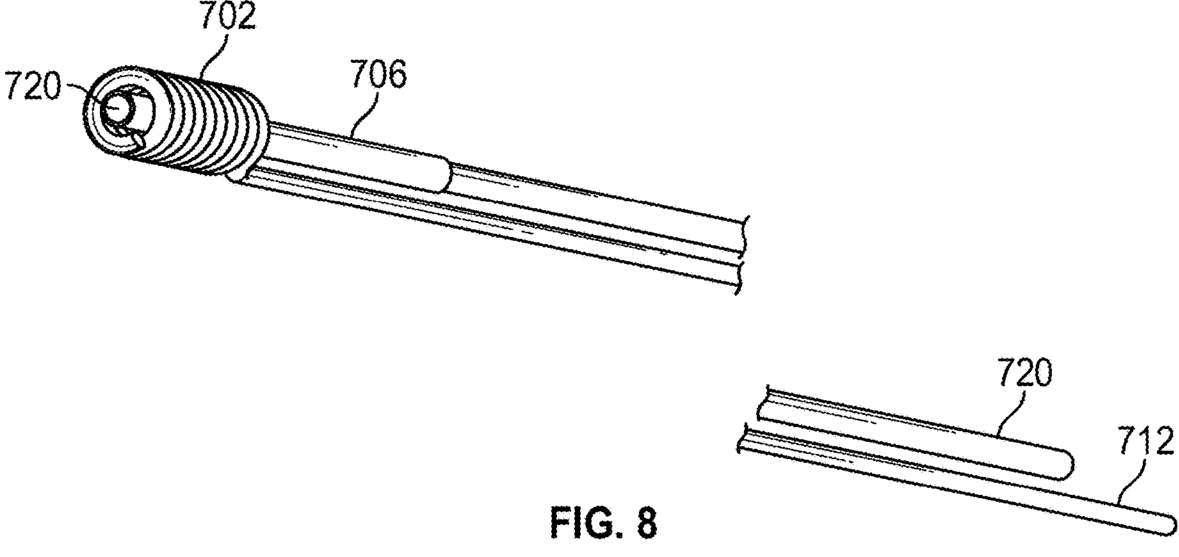
FIG. 8 is a perspective view of the system of FIG. 7.

FIGS. 7 to 9 represent an alternate embodiment of the subject treatment system. Similar to the previous embodiments, the embodiment of FIGS. 7 to 9 includes a helically coiled portion 702 at the distal end of an insulated wire 712. In addition, the distal end of the coil is not insulated and forms one electrode. Unlike the previous embodiments that included a second conductor in the form of an outer cylindrical tube, in this embodiment, the second conductor is in the form of a cylindrical central electrode 720.

The distal end of the central electrode 720 is received within the coiled portion 702 of the insulated wire. In the preferred embodiment, an insulated tube 706 surrounds the distal end of the central electrode. The insulated tube includes a plurality of holes 704 that provide additional pathways for conducting current as the coiled portion of the insulated wire erodes during use. In a preferred embodiment, an annular channel 730 is formed between the outer surface of the insulated tube 706 and the inner surface of the coiled portion 702. This channel can be used to supply conductive fluid to the distal tip of the device. Since the wire 712 is insulated, it may be possible to configure the device without the insulated tube 706.

A cylindrical outer shell 724 surrounds the distal end of the device. The shell can be formed from a metal such as stainless steel. Alternatively, the shell could be made from a non-metal such as Polyether ether ketone (PEEK) or a polyimide-based plastics such as Vespel™. The material should be heat resistant and provide some stiffness for crossing the occlusion. The proximal end portion of the outer shell (728), is formed from a more flexible material to facilitate advancement of the device through the circulatory system.

The embodiment of FIGS. 7 to 9 would be used in a manner similar to the previously discussed embodiments. Briefly, the proximal ends of the insulated wire and central electrode are connected to a power source generating pulses with a repetition rate on the order of hundreds of pulses per second. The pulses create cavitation bubbles in the conductive fluid at the distal end of the device. The cavitation bubbles create mechanical vibrations that can chip away at the occlusion.

As in the previous embodiments, during operation, the end of the coiled portion of the insulate wire will typically erode. As the wire erodes, the point at which the cavitation bubbles are generated moves circumferentially about the periphery of the central electrode. As noted above, the holes 704 in the insulated tube 706 provide sequential pathways for the current as the coiled wire erodes.

In a preferred embodiment, the central electrode 720 is removably mounted within the device. In use, after the occlusion has been opened, the central electrode can be removed providing a channel for insertion of a guidewire or other device for further treatment.

FIG. 10 illustrates a variant of the embodiment of FIGS. 7 to 9. In this embodiment, the outer surface of the insulated tube 706 includes radially projecting spacers 740. The spacers 740 function to space the central electrode 720 from the inner surface of the coiled portion 702 of insulated wire 712.

It will be understood that the foregoing is only illustrative of the principles of the invention, and that various modifications, alterations and combinations can be made by those skilled in the art without departing from the scope and spirit of the invention. For example, the foregoing principles can applied to treat occlusions formed in any part of the body. Any of the variations of the various treatment systems disclosed herein can include features described by any other treatment systems or combination of treatment systems herein. Furthermore, any of the methods can be used with any of the treatment systems disclosed. Accordingly, it is not intended that the invention be limited, except as by the appended claims. For all of the variations described above, the steps of the methods need not be performed sequentially.

What is claimed is:

1. A system for treating an occlusion within a body lumen comprising:

an insulated wire, the insulated wire having a helically coiled portion near a distal end thereof, and with a distal tip of the insulated wire having a portion of the insulation removed to define an electrode;

an elongated central electrode with a distal end thereof being received within the helically coiled portion of the insulated wire;

an insulated tube located about the distal end of the central electrode and within the helically coiled portion of the insulated wire, wherein an annular space is defined between an outer surface of the insulated tube and an inner surface of the helically coiled portion to define a fluid lumen for supplying conductive fluid to the distal tip during use; and a tubular outer shell covering the coiled portion of the insulated wire, and with proximal ends of the insulated wire and the central electrode being connectable to terminals of an electrical pulse generator, where the system is configured so that when voltage pulses are applied to the central electrode and the insulated wire, a series of cavitation bubbles are created between the electrode of the insulated wire and the central electrode and wherein as the distal tip of the insulated wire is worn away during use, the electrode of the insulated wire moves towards the proximal end of the insulated wire.

2. The system of claim 1, further comprising a pump for injecting a conductive fluid into a proximal end of the fluid lumen with the fluid exiting a distal end thereof.

3. The system of claim 1, wherein the central electrode is removable and when removed defines a lumen for receiving a guide wire.

4. The system of claim 1, wherein a distal region of the outer shell is formed from a material with greater stiffness than a proximal region of the outer shell.

5. The system of claim 1, wherein the insulated tube includes a plurality of holes arranged along the longitudinal axis thereof to provide sequential current paths between the electrode of the insulated wire and the central electrode.

6. The system of claim 1, wherein the outer surface of the insulated tube includes a plurality of radially projecting spacers to maintain separation between the central electrode and the helically coiled portion of the insulated wire.

7. The system of claim 1, further including a voltage pulse generator connected to the proximal ends of the insulated wire and the central electrode, said voltage pulse generator generating pulses having a frequency of between 14 and 800 hertz.

8. The system of claim 1, wherein the helically coiled portion of the insulated wire is configured so that as the insulated wire is worn away, the location of the generation of cavitation bubbles will rotate circumferentially about a periphery of the central electrode.

9. The system of claim 1, further including a balloon located between distal and proximal ends of the tubular outer shell for trapping debris.

10. The system of claim 1, wherein the tubular outer shell comprises a heat-resistant material.

11. The system of claim 1, wherein the tubular outer shell comprises stainless steel, polyether ether ketone, polyimide, or a combination thereof.

12. The system of claim 1, further including a voltage pulse generator connected to the proximal ends of the insulated wire and the central electrode, wherein the voltage pulse generator delivers voltage pulses at or less than 1000 volts.

13. The system of claim 1, wherein the electrical pulse generator is configured to reverse polarity of the electrodes while maintaining voltage and frequency of delivered electrical pulses.

14. The system of claim 1 wherein a distal end of the tubular outer shell further comprises a radiopaque material.

15. A system for treating an occlusion within a body lumen comprising:

an insulated wire, the insulated wire having a helically coiled portion near a distal end thereof, and with a distal tip of the insulated wire having a portion of the insulation removed to define an electrode;

an elongated central electrode with a distal end thereof being received within the helically coiled portion of the insulated wire; and a tubular outer shell covering the coiled portion of the insulated wire, and with proximal ends of the insulated wire and the central electrode being connectable to terminals of an electrical pulse generator, where the system is configured so that when voltage pulses are applied to the central electrode and the insulated wire, a series of cavitation bubbles are created between the electrode of the insulated wire and the central electrode and wherein as the distal tip of the insulated wire is worn away during use, the electrode moves towards the proximal end of the insulated wire, wherein the system does not include an insulating tube between the insulated wire and the elongated central electrode.

16. The system of claim 15, further comprising a pump for injecting a conductive fluid into a proximal end of a fluid lumen with the fluid exiting a distal end thereof.

17. The system of claim 15, wherein the central electrode is removable and when removed defines a lumen for receiving a guide wire.

18. The system of claim 15, further including a voltage pulse generator connected to proximal ends of the insulated wire and the central electrode, said voltage generator generating pulses having a frequency of between 14 and 800 hertz.

* * * * *